US010835225B2

(12) United States Patent
Walters et al.

(10) Patent No.: US 10,835,225 B2
(45) Date of Patent: Nov. 17, 2020

(54) VASCULAR LOCATING SYSTEMS AND METHODS OF USE

(71) Applicant: Arrow International, Inc., Wayne, PA (US)

(72) Inventors: Greg Walters, Exton, PA (US); Joseph T. Grintz, Glenmoore, PA (US); Julie Lin, West Chester, PA (US)

(73) Assignee: Arrow International, Inc., Wayne, PA (US)

( * ) Notice: Subject to any disclaimer, the term of this patent is extended or adjusted under 35 U.S.C. 154(b) by 125 days.

(21) Appl. No.: 16/245,906

(22) Filed: Jan. 11, 2019

(65) Prior Publication Data
US 2019/0142404 A1 May 16, 2019

Related U.S. Application Data

(60) Continuation of application No. 15/385,656, filed on Dec. 20, 2016, now Pat. No. 10,182,804, which is a
(Continued)

(51) Int. Cl.
*A61B 17/00* (2006.01)
*A61B 90/00* (2016.01)
(Continued)

(52) U.S. Cl.
CPC .......... *A61B 17/0057* (2013.01); *A61B 90/39* (2016.02); *A61M 25/09* (2013.01); *A61M 29/02* (2013.01); *A61B 2017/00623* (2013.01); *A61B 2017/00654* (2013.01); *A61B 2017/00672* (2013.01); *A61B 2090/062* (2016.02);
(Continued)

(58) Field of Classification Search
CPC ...... A61B 17/0057; A61B 2017/00654; A61B 2017/00659; A61B 2017/00575; A61B 2017/00579; A61B 2017/00592; A61B 2017/00597; A61B 2017/00601; A61B 2017/00606; A61B 2017/0061; A61B 2017/00615; A61B 2017/00628;
(Continued)

(56) References Cited

U.S. PATENT DOCUMENTS 4,760,847 A   8/1988 Vaillancourt
5,021,059 A   6/1991 Kensey et al.
(Continued)

FOREIGN PATENT DOCUMENTS

EP       0664687 B2    8/2003

OTHER PUBLICATIONS

Nash et al., The Angio-Seal Hemostatic Puncture Closure Device, Concept and Experimental Results,Herz Urban & Vogel, 1999, pp. 597-606, Kensey Nash Corporation, Exton, Pennsylvania, USA.
(Continued)

*Primary Examiner* — Wade Miles
(74) *Attorney, Agent, or Firm* — Offit Kurman P.C.; Gregory A. Grissett

(57) ABSTRACT

Disclosed are puncture sealing systems and methods of locating a puncture site within a vessel. The systems can include puncture locating dilators and access sheaths that are configured to locate the puncture site within a vessel so that the position of the puncture site relative to a distal end of the access sheath is known during a puncture sealing procedure.

10 Claims, 14 Drawing Sheets

Related U.S. Application Data division of application No. 14/063,522, filed on Oct. 25, 2013, now Pat. No. 9,554,785.

(60) Provisional application No. 61/846,217, filed on Jul. 15, 2013, provisional application No. 61/745,006, filed on Dec. 21, 2012.

(51) Int. Cl.
*A61M 25/09* (2006.01)
*A61M 29/02* (2006.01)

(52) U.S. Cl.
CPC ............... *A61B 2090/3904* (2016.02); *A61B 2090/3966* (2016.02)

(58) Field of Classification Search
CPC .. A61B 2017/00632; A61B 2017/1205; A61B 2017/00672
See application file for complete search history.

(56) References Cited

U.S. PATENT DOCUMENTS

| | | | |
|---|---|---|---|
| 5,193,106 | A | 3/1993 | DeSena |
| 5,282,827 | A | 2/1994 | Kensey et al. |
| 5,292,309 | A | 3/1994 | Van Tassel et al. |
| 5,306,254 | A | 4/1994 | Nash et al. |
| 5,324,306 | A | 6/1994 | Makower et al. |
| 5,441,517 | A | 8/1995 | Kensey et al. |
| 5,469,847 | A | 11/1995 | Zinreich et al. |
| 5,755,746 | A | 5/1998 | Lifshey et al. |
| 6,090,130 | A | 7/2000 | Nash et al. |
| 6,425,911 | B1 | 7/2002 | Akerfeldt et al. |
| 6,494,848 | B1 | 12/2002 | Sommercom et al. |
| 6,682,489 | B2 | 1/2004 | Tenerz et al. |
| 7,044,916 | B2 | 5/2006 | Tenerz et al. |
| 7,073,509 | B2 | 7/2006 | Tenerz et al. |
| 7,285,097 | B2 | 10/2007 | Tenerz et al. |
| 7,648,493 | B2 | 1/2010 | Forsberg et al. |
| 7,753,935 | B2 | 7/2010 | Brett et al. |
| 7,850,654 | B2 | 12/2010 | Belhe et al. |
| 8,273,094 | B2 | 9/2012 | Belhe et al. |
| 8,382,793 | B2 | 2/2013 | Egnelov et al. |
| 8,401,620 | B2 | 3/2013 | Velusamy et al. |
| 9,554,785 | B2 * | 1/2017 | Walters ................. A61B 90/39 |
| 2001/0044639 | A1 | 11/2001 | Levinson |
| 2004/0147846 | A1 | 7/2004 | Mueller, Jr. et al. |
| 2005/0107750 | A1 * | 5/2005 | Barongan ......... A61M 25/0662 604/264 |
| 2005/0107820 | A1 | 5/2005 | Forsberg et al. |
| 2006/0282106 | A1 | 12/2006 | Cole et al. |
| 2007/0123936 | A1 | 5/2007 | Goldin et al. |
| 2008/0306509 | A1 | 12/2008 | Osborne |
| 2008/0319475 | A1 | 12/2008 | Clark et al. |
| 2009/0082784 | A1 | 3/2009 | Meissner et al. |
| 2009/0156929 | A1 | 6/2009 | Franco |
| 2011/0054456 | A1 | 3/2011 | Thompson et al. |
| 2011/0172767 | A1 | 7/2011 | Rathi et al. |
| 2012/0203328 | A1 | 8/2012 | Yribarren |
| 2012/0283770 | A1 | 11/2012 | Kramer et al. |
| 2012/0296275 | A1 | 11/2012 | Martin et al. |
| 2013/0245644 | A1 * | 9/2013 | Tegels ................ A61B 17/0057 606/144 |
| 2017/0100113 | A1 | 4/2017 | Walters et al. |

OTHER PUBLICATIONS

St. Jude Medical, Angio-Seal Vascular Closure Device Millennium Platform, Brochure, 2001, 10 pp.

* cited by examiner

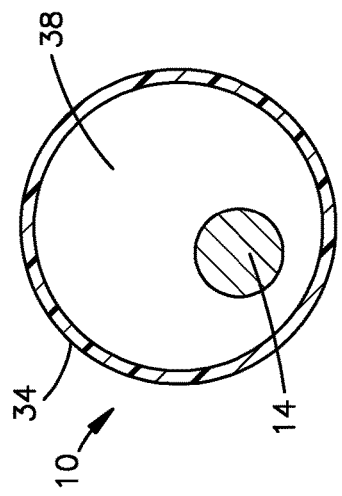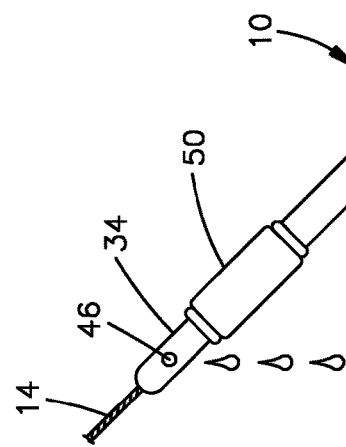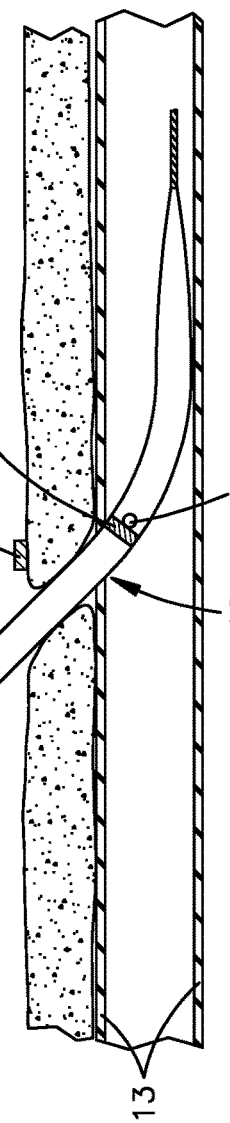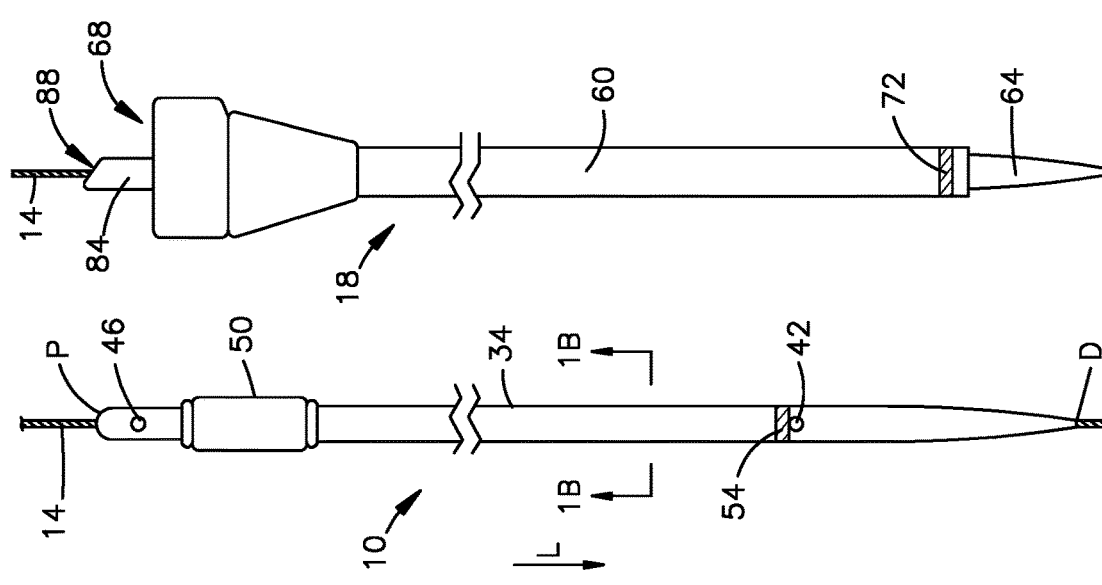

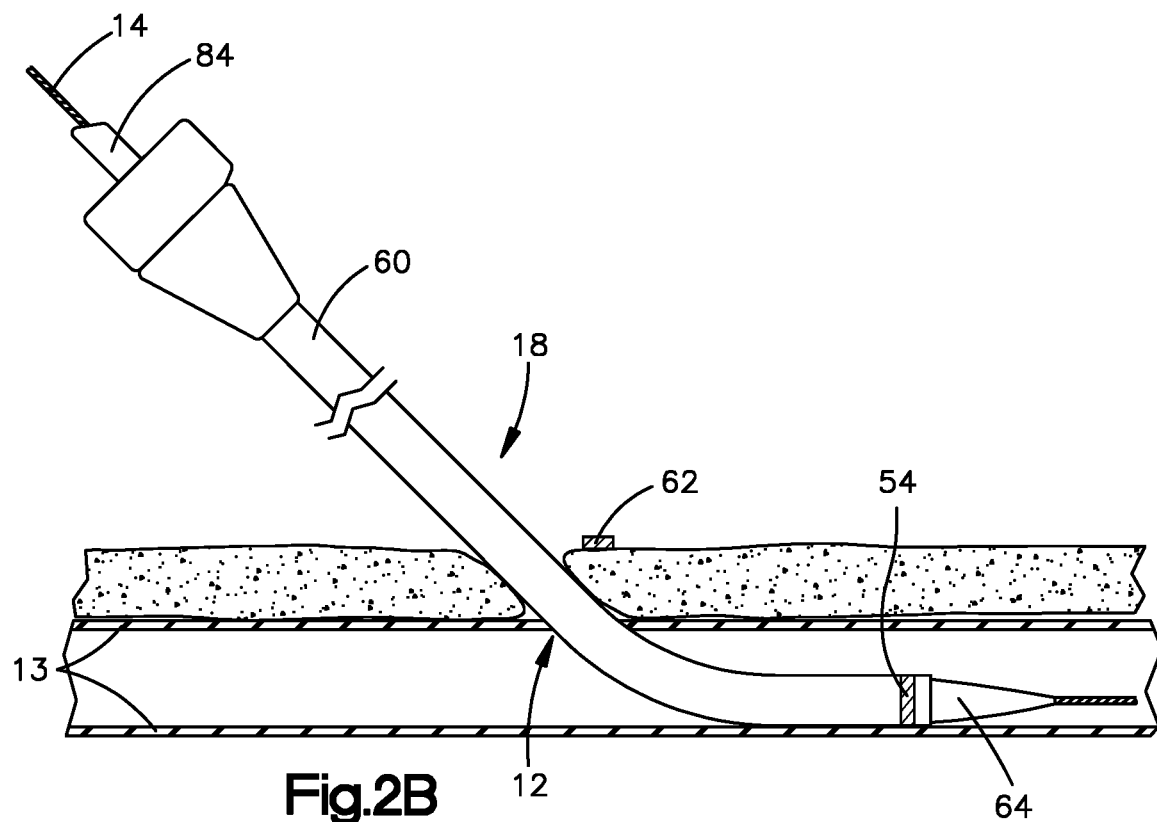
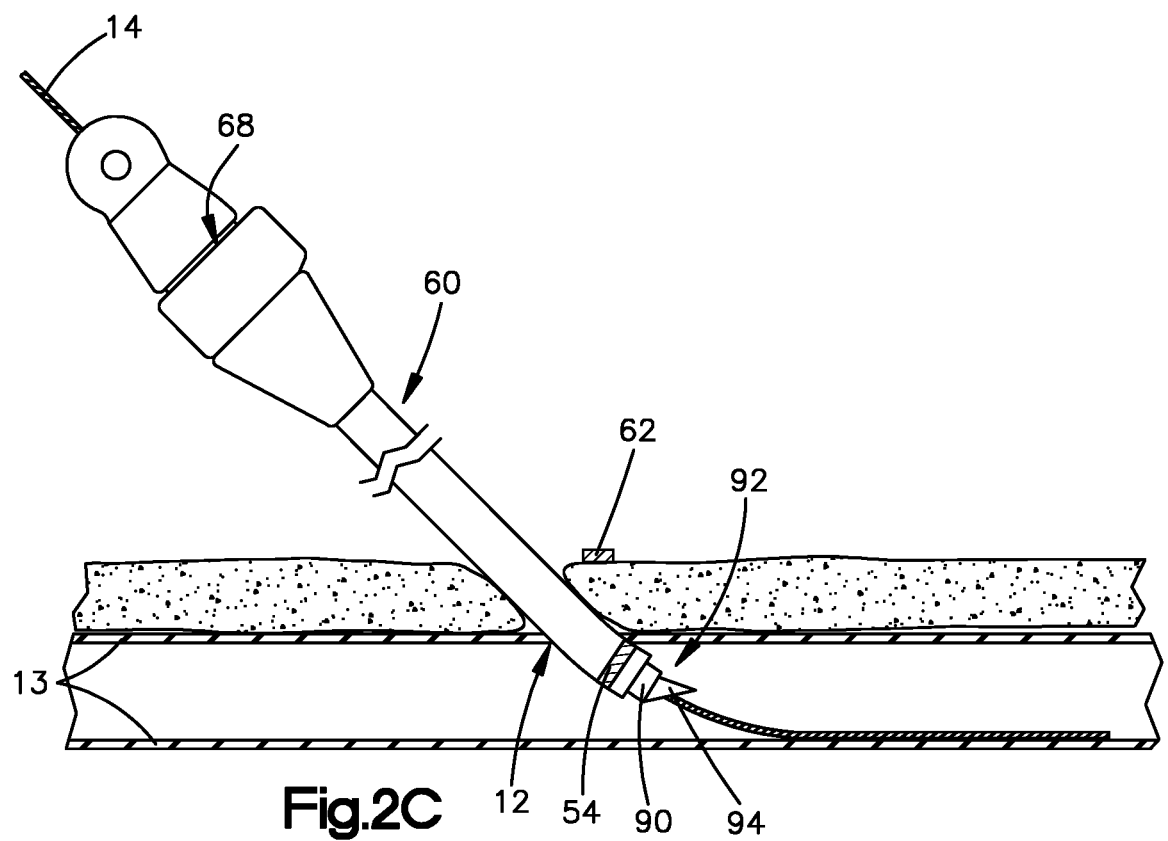

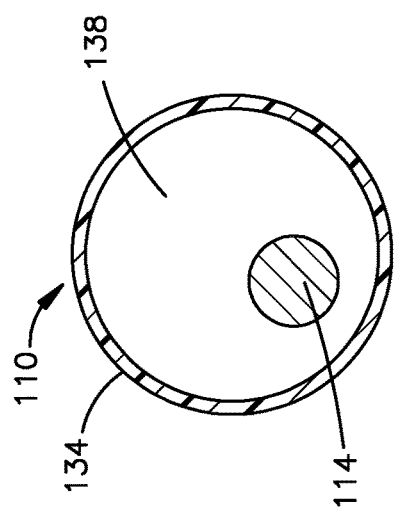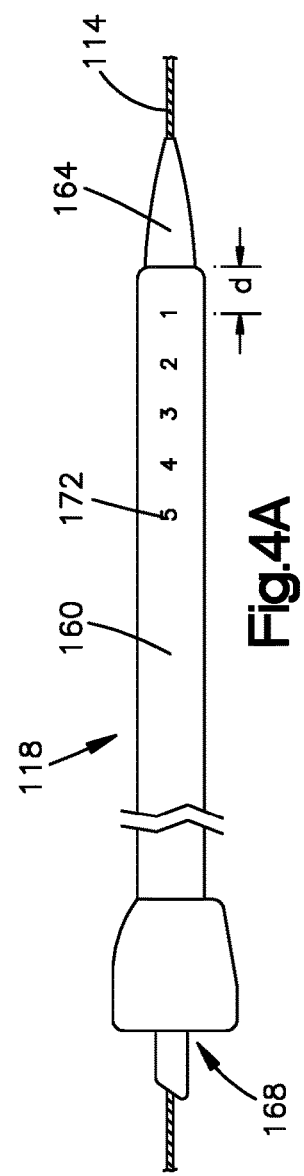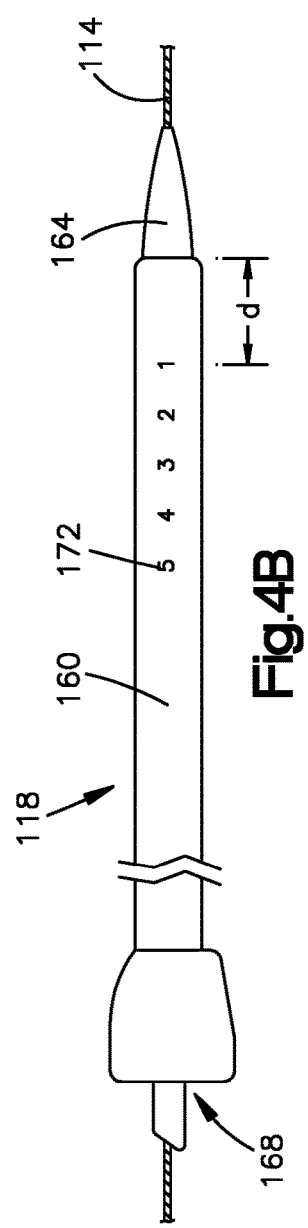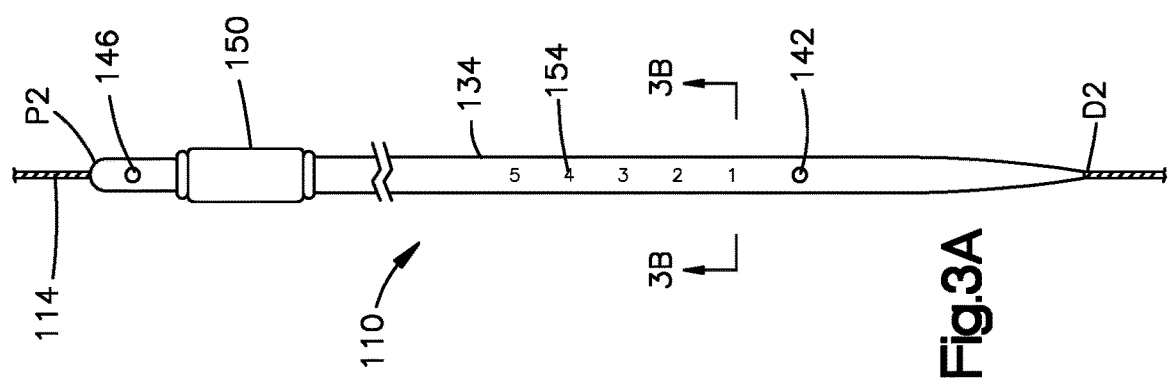

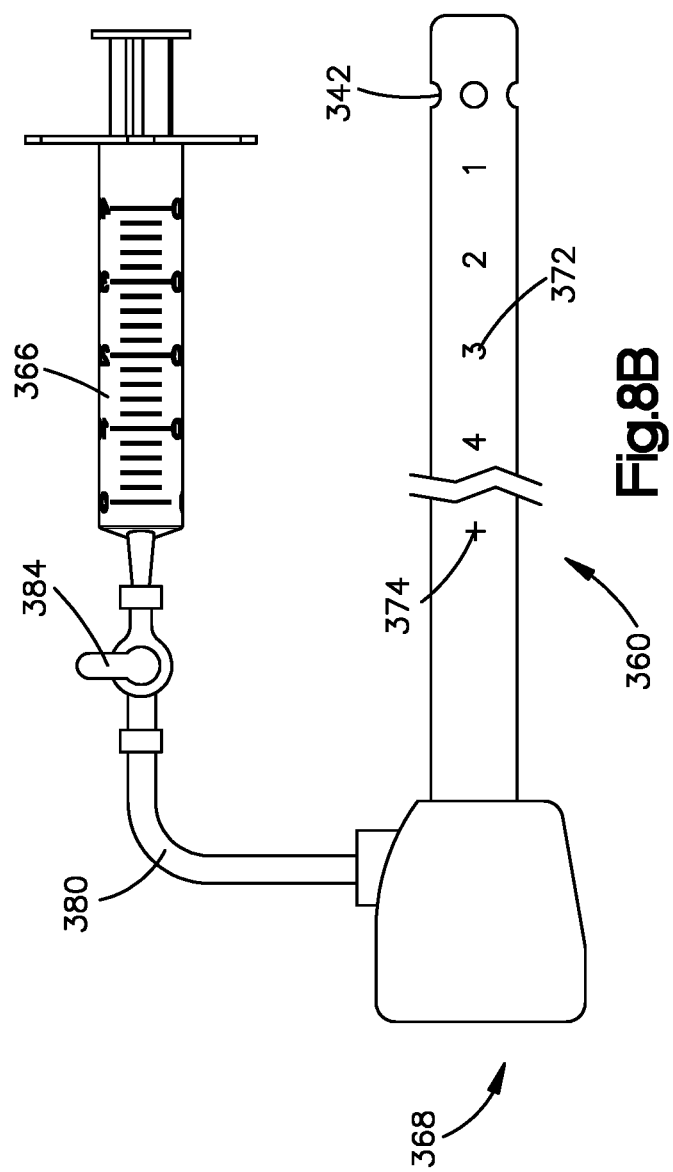
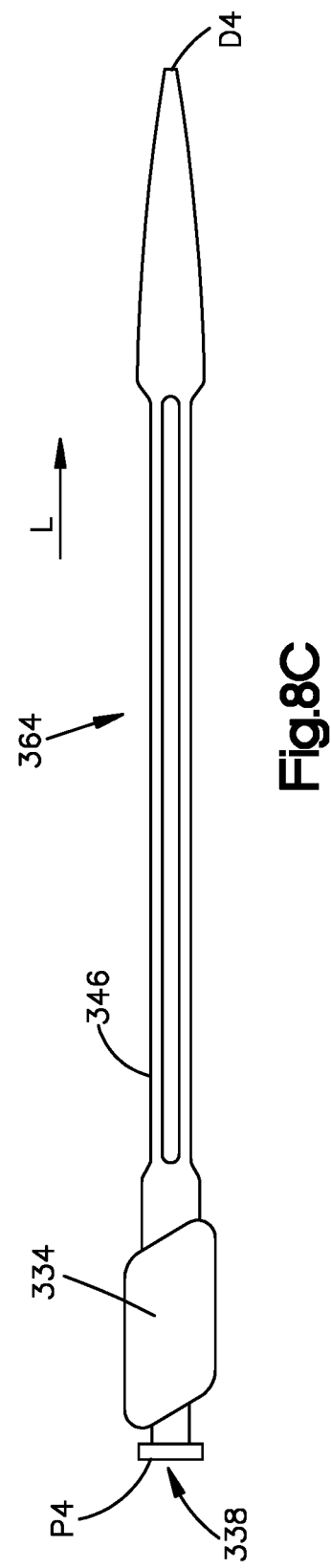
Fig.8B
Fig.8C

VASCULAR LOCATING SYSTEMS AND METHODS OF USE

CROSS REFERENCE TO RELATED APPLICATIONS

This application is a continuation of U.S. application Ser. No. 15/385,656, filed Dec. 20, 2016, which is a divisional of U.S. application Ser. No. 14/063,522 filed Oct. 25, 2013, issued Jan. 31, 2017 as U.S. Pat. No. 9,554,785, which claims priority to and the benefit of U.S. Provisional Application Ser. No. 61/846,217, filed Jul. 15, 2013, and U.S. Provisional Application Ser. No. 61/745,006 filed Dec. 21, 2012, the contents of each of which are hereby incorporated by reference as if set forth in their entirety herein.

BACKGROUND

During the use of vascular closure systems after vascular interventions, it is often important to know the location of a puncture in the vessel, and in particular, providing for exact placement of vascular sheaths. Typically, a "blood flashback" method is used to position a vascular device, but this technique is not feasible with catheters whose size is similar to the vessel internal diameter (ID) due to the limited flow possible.

SUMMARY

In an embodiment of the invention, a method of locating a puncture site in a vessel of a patient, can comprise the steps of inserting a guide wire through the puncture site and into the vessel such that a portion of the guide wire protrudes from the vessel; inserting a proximal end of the guide wire into a distal end of a dilator, the dilator having an inlet hole, an outlet hole in fluid communication with the inlet hole, and a radiopaque marker proximate to the inlet hole; moving the dilator along the guide wire until the distal end of the dilator and the inlet hole enter the vessel such that blood flows into the inlet hole and out the outlet hole to thereby locate a position of the puncture site; after the position of the puncture site has been located, determining a position of the radiopaque marker of the dilator on an imaging device; and positioning an external marker on the patient that corresponds with the position of the radiopaque marker of the dilator determined on the imaging device to thereby provide a visual indication of the puncture site location after the dilator is removed from the guide wire.

In accordance with another embodiment of the invention, a method of locating a puncture site in a vessel of a patient, can comprise the steps of inserting a guide wire through the puncture site and into the vessel such that a portion of the guide wire protrudes from the vessel; inserting a proximal end of the guide wire into a distal end of a sheath dilator that is coupled within an access channel of a sheath body, at least one of the sheath dilator and the sheath body having an inlet hole and an outlet hole in fluid communication with the inlet hole; moving the sheath dilator and sheath body combination along the guide wire until the distal end of the sheath dilator and the inlet hole enter the vessel such that blood flows into the inlet hole and out the outlet hole to thereby determine a position of the puncture site; and noting a first visible marking of a plurality of markings on the sheath body that is adjacent the patient's skin when the blood flows out the outlet hole.

In accordance with yet another embodiment of the invention, a method of locating a puncture site in a vessel of a patient, can comprise the steps of inserting a guide wire through the puncture site and into the vessel such that a portion of the guide wire protrudes from the vessel; inserting a proximal end of the guide wire into a distal end of a sheath dilator that is coupled within an access channel of a sheath body, the sheath dilator having an inlet hole; moving the sheath dilator and sheath body combination distally along the guide wire until the distal end of the sheath dilator and the inlet hole enter the vessel; confirming that the inlet hole is within the vessel by drawing fluid from the vessel with a syringe that is in communication with the inlet hole; slightly withdrawing the sheath dilator and sheath body combination proximally along the guide wire; actuating the syringe to determine whether the inlet hole is within the vessel; repeating the withdrawing and actuating steps until the inlet hole is external to the vessel; after the repeating step, slightly move the sheath dilator and sheath body combination distally along the guide wire to thereby position the inlet hole within the vessel; and noting a first visible marking of a plurality of markings on the sheath body that is adjacent the patient's skin when the inlet hole is positioned in the vessel.

BRIEF DESCRIPTION OF THE DRAWINGS

The foregoing summary, as well as the following detailed description of example embodiments of the application, will be better understood when read in conjunction with the appended drawings, in which there is shown in the drawings example embodiments for the purposes of illustration. It should be understood, however, that the application is not limited to the precise systems and methods shown. In the drawings:

FIG. 1A is a top plan view, showing a puncture locating dilator of a puncture sealing system in accordance with an embodiment of the invention, the puncture locating dilator having a dilator body that defines a blood inlet hole, a blood outlet hole, and a radiopaque marker adjacent the blood inlet hole;

FIG. 1B is a cross-sectional view of the puncture locating dilator shown in FIG. 1A through the line 1B-1B;

FIG. 1C is a top plan view, showing an access sheath of the puncture sealing system shown in FIG. 1A, the access sheath having a sheath body and a sheath dilator coupled within an access channel of the sheath body;

FIG. 2A is a schematic showing the puncture locating dilator of FIG. 1 positioned such that the inlet hole is disposed within a vessel proximate to a puncture site and such that an external radiopaque marker placed on the skin is aligned with the radiopaque marker on the dilator body;

FIG. 2B is a schematic showing the access sheath of FIG. 1C being inserted into the vessel;

FIG. 2C is a schematic showing the sheath dilator removed from the access channel and the sheath body positioned such that a radiopaque marker near a distal end of the sheath body is aligned with the external radiopaque marker;

FIG. 3A is a top plan view, showing a puncture locating dilator of a puncture sealing system in accordance with another embodiment of the invention, the puncture locating dilator having dilator body that defines a blood inlet hole, a blood outlet hole, and a plurality of depth markings spaced from each other between the inlet and outlet holes;

FIG. 3B is a cross-sectional view of the puncture locating dilator shown in FIG. 3A through the line 3B-3B;

FIG. 4A is a top plan view, showing an access sheath of the puncture sealing system shown in FIG. 3A, the access sheath having a sheath body and a sheath dilator coupled within an access channel of the sheath body, the sheath body defining a plurality of depth markings that correspond to the depth markings on the puncture locating dilator shown in FIG. 3A;

FIG. 4B is a top plan view, showing an access sheath in accordance with another embodiment, the access sheath having a sheath body that defines a distance measured from a distal end of the sheath body to a first depth marker on the sheath body that is greater than that of the access sheath shown in FIG. 4A;

FIG. 8B is a top plan view of the sheath body shown in FIG. 8A, the sheath body including four blood inlet holes, a syringe in communication with the blood inlet holes, and a plurality of depth markings spaced between the syringe and blood inlet holes;

FIG. 8C is a top plan view of the sheath dilator shown in FIG. 8A, the sheath dilator having a dilator body that defines four blood flow channels;

DETAILED DESCRIPTION OF ILLUSTRATIVE EMBODIMENTS

Figure 5A:
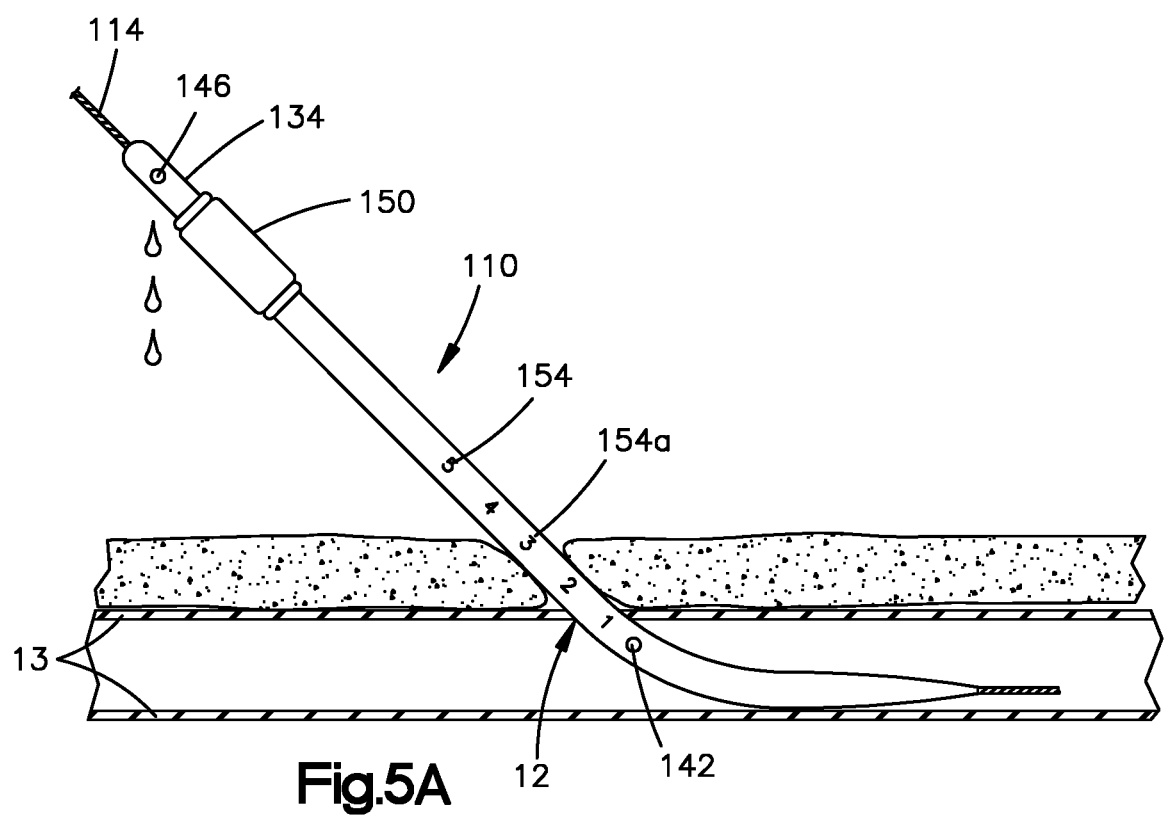
FIG. 5A is a schematic showing the puncture locating dilator of FIG. 3A positioned such that the inlet hole is disposed within a vessel proximate to a vessel puncture and at least one of the markings being visible above the surface of the skin.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Referring to FIGS. 1A-2C, a puncture sealing system in accordance with an embodiment of the invention can include a puncture locating dilator 10 that is configured to locate a puncture site 12 in a vessel 13 of a patient using radiopaque markers. As shown in FIGS. 1A and 1B, the puncture locating dilator 10 is configured to be moved along a guide wire 14 toward the puncture site 12 such that the puncture locating dilator 10 enters the vessel 13 through the puncture site 12. As the puncture locating dilator 10 enters the vessel 13 the puncture locating dilator 10 dilates the puncture site 12. As shown in FIG. 1C, the puncture sealing system can further include an access sheath 18 that is also configured to be moved along the guide wire 14 toward the puncture site 12 and into the vessel 13 so as to further dilate the puncture site 12 and subsequently provide access to the vessel 13. The access sheath 18 can then receive a sealing device that is configured to seal the puncture site 12. It should be appreciated, however, that the system can include additional dilators that have cross-sectional diameters that are different (e.g. greater) than the diameter of the locating dilator 10 but less than that of the access sheath 18 so that the puncture site 12 can be gradually dilated and prepared for the access sheath 18. Both the locating dilator 10 and the access sheath 18 include a respective radiopaque marker that is configured to aid in locating the puncture site 12.

As shown in FIGS. 1A and 1B, the puncture locating dilator 10 includes a dilator body 34 that is elongate along a first direction L and defines a proximal end P and a distal end D that is spaced from the proximal end P along the first direction L. As shown in FIGS. 1A and 1B, the puncture locating dilator 10 defines a guide channel 38 that extends through the dilator body 34 along the first direction L from the distal end D through to the proximal end P. The guide channel 38 is configured to receive the guide wire 14 such that the puncture locating dilator 10 can be moved along the guide wire 14 toward the puncture site 12. The guide channel 38 at the distal and proximal ends D and P can have a diameter that is substantially equal to that of the guide wire 14 so that the puncture locating dilator 10 can move along the guide wire 14 in a controlled manner. As shown in FIG. 1A, the puncture locating dilator 10 can further define a blood inlet hole 42 that extends through the dilator body 34 along a direction that is transverse to the first direction L, and a blood outlet hole 46 that extends through the dilator body 34 proximal to the blood inlet hole 42. The blood inlet hole 42 and the blood outlet hole 46 are in fluid communication with each other such that when the blood inlet hole 42 enters the vessel 13, blood from the vessel 13 will enter the blood inlet hole 42 and exit the blood outlet hole 46 to thereby indicate that the blood inlet hole 42 has entered the vessel 13. In this way, a position of the puncture site 12 can be located or otherwise determined. In the illustrated embodiment, the blood inlet and outlet holes 42 and 46 extend into the guide channel 38 such that blood entering the blood inlet hole 42 will travel through the guide channel 38, around the guide wire 14, and out the blood outlet hole 46. It should be appreciated, however, that in some embodiments, the guide channel 38 and the channel through which the blood flows can be separate and distinct from each other, as desired.

With continued reference to FIG. 1A, the puncture locating dilator 10 can further include a hub 50 that extends radially out from the dilator body 34 between the inlet and outlet holes 42 and 46. The hub 50 can be configured as a handle that can be firmly grasped to thereby move the puncture locating dilator 10 along the guide wire 14. It should be appreciated, however, that the hub 50 can be located anywhere along the dilator body 34 as desired.

With continued reference to FIG. 1A, the puncture locating dilator 10 can further include a radiopaque marker 54 that is proximate to the blood inlet hole 42. In the illustrated embodiment, the radiopaque marker 54 is a band that extends around the dilator body 34 proximal to the blood inlet hole 42. It should be appreciated, however, that the radiopaque marker 54 can be distal to the blood inlet hole 42 as desired and can have other configurations as desired. For example, the radiopaque marker 54 can be internally located rather than as an external band, as desired or can be a ball that is bored into a side of the body 34. The radiopaque marker 54 can be used to angiographically locate the puncture site 12. That is, after a position of the puncture site 12 has been located with the blood inlet hole 42, a position of the radiopaque marker 54 can be determined on an imaging device such as a fluoroscope. An external marker 62 can then be positioned on the patient that corresponds with the position of the radiopaque marker 54 determined on the imaging device to thereby provide a visual indication of the puncture site location after the puncture locating dilator 10 has been removed from the guide wire 14. As shown in FIG. 2A, the external marker 62 can be a radiopaque sticker that is placed directly on the patient's skin as desired. It should be appreciated, however, that the external marker 62 can be placed on the patient but not directly to the patient's skin as desired. Furthermore, it should be appreciated, that the external marker 62 can have other configurations as desired. For example, the external marker 62 can be a tag, card, clip, etc.

Now referring to FIG. 1C, the access sheath 18 includes a sheath body 60 that is elongate along the first direction L and a sheath dilator 64 that is coupled within an access channel 68 of the sheath body 60. The access channel 68 extends through the sheath body 60 from a proximal end through to a distal end of the sheath body 60 and is configured to provide an access path to the puncture site 12 after the sheath dilator 64 has been removed from the access channel 68. The access sheath 18 like the puncture locating dilator 10 is configured to be moved along the guide wire 14 toward the puncture site 12 such that the distal end of the access sheath 18 enters the vessel 13.

With continued reference to FIG. 1C, the access sheath 18 further includes a radiopaque marker 72 on the sheath body 60 proximate to a distal end of the sheath body 60. In the illustrated embodiment, the radiopaque marker 72 is a band that extends around the sheath body 60. It should be appreciated, however, that the radiopaque marker 72 can have other configurations as desired so long as it can be seen on an imaging device. The radiopaque marker 72 can be used to position the sheath body 60. For example, the sheath body 60 can be positioned such that the radiopaque marker 72 is aligned with the external radiopaque marker 62. As with the positioning of the puncture locating dilator 10, the access sheath 18 or at least the sheath body 60 can be positioned using the imaging device. When aligned, the appropriate amount of sheath body 60 will be disposed within the vessel 13 or at least the closure device will be properly positioned.

Similar to the puncture locating dilator 10, the sheath dilator 64 includes a dilator body 84 that is elongate along the first direction L and defines a guide channel 88 that extends through the dilator body 34 along the first direction L from a distal end through to a proximal end of the dilator body 84. The guide channel 88 is configured to receive the guide wire 14 such that the access sheath 18 can be moved along the guide wire 14 toward the puncture site 12. The guide channel 88 at the distal and proximal ends of the dilator body 84 can have a diameter that is substantially equal to that of the guide wire 14 so that the access sheath 18 can move along the guide wire 14 in a controlled manner. Once the access sheath 18 has been inserted into the vessel 13, the sheath dilator 64 can be pulled proximally from the access channel 68. At this point, a closure device 90 can be inserted into the access channel 68. And when the closure device 90 is properly positioned using the radiopaque marker 72, the puncture site can be sealed.

Now referring to FIGS. 2A-2C, the guide wire can be inserted through the puncture site 12 and into the vessel 13 such that a portion of the guide wire 14 protrudes from the vessel 13. Once the guide wire 14 is positioned, a proximal end of the guide wire 14 can be inserted into the distal end of the puncture locating dilator 10. As shown in FIG. 2A, the puncture locating dilator 10 can then be moved along the guide wire 14 until the distal end of the puncture locating dilator 10 and the blood inlet hole 34 enter the vessel 13 such that blood flows into the inlet hole 42 and out the outlet hole 46 to thereby locate a position of the puncture site 12. The position of the puncture site 12 can be confirmed via feedback of blood flow exiting the blood outlet hole 46 by alternatingly inserting and retracting the puncture locating dilator 10. As shown in FIG. 2A, after the position of the puncture site 12 has been located, a position of the radiopaque marker 54 of the dilator 10 can be determined on an imaging device and an external marker 62 can be positioned on the patient. The external marker 62 can be positioned such that it corresponds with the position of the radiopaque marker 54 of the dilator 10 to thereby provide a visual indication of the puncture site location after the dilator 10 is removed from the guide wire 14. It should be appreciated, that in some embodiments, the puncture locating dilator 10 can be positioned over the guide wire 14 prior to the guide wire being inserted into the vessel 13.

As shown in FIG. 2B, after the puncture locating dilator 10 has been removed from the guide wire 14 and any subsequent dilators have been removed, the access sheath 18 can be moved along the guide wire 14 toward the puncture site 12 such that the distal end of the access sheath 18 enters the vessel 13 through the puncture site 12. In particular, the proximal end of the guide wire 14 is inserted into the distal end of the sheath dilator 64. And then the sheath body 60 and sheath dilator 64 can be moved together along the guide wire 14 toward the puncture site 12. Once inserted, the sheath dilator 64 can be pulled proximally such that the sheath dilator 64 is removed from the access channel 68.

After the sheath dilator 64 has been removed, access for a vascular closure procedure as is detailed in PCT/US2012/061855, the disclosure of which is hereby incorporated by reference herein, can be performed through the access channel 68. Therefore as shown in FIG. 2C, a closure device 90 can be moved into the access channel 68 until a distal portion 92 (e.g. at least a portion of a toggle 94) of the closure device 90 is distal to the distal end of the sheath body 60. The access sheath 18 can then be moved such that the radiopaque marker 72 proximate to the distal end of the sheath body 60 is aligned with the external marker 62. The radiopaque markers 72 and 62 can be aligned by viewing the markers 62 and 72 on an imaging device such as a fluoroscope while the access sheath 18 and thus the closure device 90 is being positioned. It should be appreciated, however, that while the closure device 90 is preferably moved into the access channel 68 prior to the positioning of the access sheath 18 such that the radiopaque marker 72 is aligned with the external marker 62, the closure device 90 can be moved into the access channel 68 after the positioning of the access sheath 18, as desired. When the access sheath 18 is properly positioned, the closure device 90 will be positioned such that the sealing procedure can be completed. It should be appreciated, that while in the illustrated embodiment, the radiopaque marker 72 is on the sheath body 60, in some embodiments, the radiopaque marker 72 can be on the closure device 90, as desired. Furthermore, it should be appreciated, that in such embodiments, the access sheath 18 can be pulled completely out of the vessel when the closure device 90 is properly positioned (see e.g. FIGS. 10A and 10B).

Now in reference to FIGS. 3A-5C, a puncture sealing system in accordance with another embodiment of the invention can include a puncture locating dilator 110 that is configured to locate the puncture site 12 in the vessel 13 of a patient using depth markings. The depth markings of this embodiment can either be used alone or in combination with the radiopaque markers of the embodiment shown in FIGS. 1A-2C. As shown in FIGS. 4A and 4B, the system can further include an access sheath 118 that also includes depth markings that correspond to the depth markings of the puncture locating dilator 110. The system including the puncture locating dilator 110 and the access sheath 118 are substantially similar to the puncture locating dilator 10 and the access sheath 18 shown in FIGS. 1A-2C, and operate in a similar manner unless otherwise described.

As shown in FIGS. 3A and 3B, like the puncture locating dilator 10, the puncture locating dilator 110 includes a dilator body 134 that is elongate along the first direction L and defines a proximal end $P_2$ and a distal end $D_2$ that is spaced from the proximal end $P_2$ along the first direction L. As shown in FIGS. 3A and 3B, the puncture locating dilator 110 defines a guide channel 138 that extends through the dilator body 134 along the first direction L from the distal end $D_2$ through to the proximal end $P_2$. The guide channel 138 is configured to receive the guide wire 114 such that the puncture locating dilator 110 can be moved along the guide wire 114 toward the puncture site 12. The guide channel 138 at the distal and proximal ends $D_2$ and $P_2$ can have a diameter that is substantially equal to that of the guide wire 114 so that the puncture locating dilator 110 can move along the guide wire 114 in a controlled manner. As shown in FIG. 3A, the puncture locating dilator 110 can further define a blood inlet hole 142 that extends through the dilator body 134 along a direction that is transverse to the first direction L, and a blood outlet hole 146 that extends through the dilator body 134 proximal to the blood inlet hole 142. The blood inlet hole 142 and the blood outlet hole 146 are in fluid communication with each other such that when the blood inlet hole 142 enters the vessel 13, blood from the vessel 13 will enter the blood inlet hole 142 and exit the blood outlet hole 146 to thereby indicate that the blood inlet hole 142 has entered the vessel 13. In this way, a position of the puncture site 12 can be located or otherwise determined. In the illustrated embodiment, the blood inlet and outlet holes 142 and 146 extend into the guide channel 138 such that blood entering the blood inlet hole 142 will travel through the guide channel 138, around the guide wire 114, and out the blood outlet hole 146.

With continued reference to FIG. 3A, the puncture locating dilator 110 can further include a hub 150 that is similar to hub 50. As shown in FIG. 3A, the hub 150 extends radially out from the dilator body 134 between the inlet and outlet holes 142 and 146. The hub 150 can be configured as a handle that can be firmly grasped to thereby move the puncture locating dilator 110 along the guide wire 114.

With continued reference to FIG. 3A, the puncture locating dilator 110 can further include a plurality of depth markings 154 spaced from each other along the first direction L between the inlet and outlet holes 142 and 146. The depth markings 154 can be used to visually note the depth or otherwise the location of the puncture site 12 of the vessel 13 when the puncture locating dilator 110 has been positioned within the vessel. In the illustrated embodiment, the depth markings 154 are numbers on the dilator body 134. It should be appreciated, however, that the depth markings 154 can have other configurations as desired. For example, the depth markings can be configured as symbols as desired. The depth markings 154 can be used to locate the puncture site 12. That is, after a position of the puncture site 12 has been located with the blood inlet hole 142, a position of a first visible marking of the plurality of depth markings 154 on the dilator that is adjacent the patient's skin can be noted when the blood flows. Therefore, the position of the puncture site 12 can be known for the remainder of the procedure. The noted first marking can be noted with a sticker that is placed directly on the patient's skin as desired. It should be appreciated, however, that the first depth marking can be noted using other configurations as desired. For example, the first depth marking can be noted with a tag, card, clip, etc.

Now referring to FIG. 4A, the access sheath 118 includes a sheath body 160 that is elongate along the first direction L and a sheath dilator 164 that is coupled within an access channel 168 of the sheath body 160. The access channel 168 extends through the sheath body 160 from a proximal end through to a distal end of the sheath body 160 and is configured to provide an access path to the puncture site 12 after the sheath dilator 164 has been removed from the access channel 168. The access sheath 118 like the puncture locating dilator 110 is configured to be moved along the guide wire 114 toward the puncture site 12 such that the distal end of the access sheath 118 enters the vessel 13.

With continued reference to FIG. 4A, the access sheath 18 further includes a plurality of depth markings 172 spaced from each other along the first direction L on the sheath body 160. The depth markings 172 correspond to the depth markings 154 on the puncture locating dilator 110 such that as the access sheath 18 is inserted into the vessel 13 the location of the distal end of the access sheath 118 relative to the puncture site 12 can be known because of the depth markings 172. In the illustrated embodiment, the depth markings 172 are numbers. It should be appreciated, however, that the depth markings 172 can have other configurations as desired so long as they somehow correspond to the depth markings 154. The depth markings 172 can be used to position the sheath body 160 so that a closure device 190 that is to be moved into the access channel 168 will be properly positioned for sealing of the puncture site 12. For example, the sheath body 160 can be positioned such that a first marking of the depth markings 172 that corresponds to the noted first visible marking on the dilator 110 is the first visible marking on the access sheath 118. When the first visible marking of the access sheath 118 corresponds to the noted first visible marking on the puncture locating dilator 110, the appropriate amount of sheath body 160 will be disposed within the vessel 13. It should be appreciated, however, that in some embodiments, the depth markings 172 can be placed on the closure device 190 rather than the sheath body 160.

As shown in FIGS. 4A and 4B, a distance d between a distal end of the access sheath 118 and a first marking of the plurality of depth markings 172 can be varied. For example, the distance d in the embodiment shown in FIG. 4B is greater than that of the embodiment shown in FIG. 4A. Therefore, different access sheaths 118 can be used depending on the application. For example, in a procedure using the closure device illustrated in the 855 application, the access sheath 118 shown in FIG. 4A may be used.

The sheath dilator 164 is similar to the sheath dilator 64 and operates in a similar manner. Therefore, once the access sheath 118 has been inserted into the vessel 13, the sheath dilator 164 can be pulled proximally from the access channel 168.

Figure 5B:
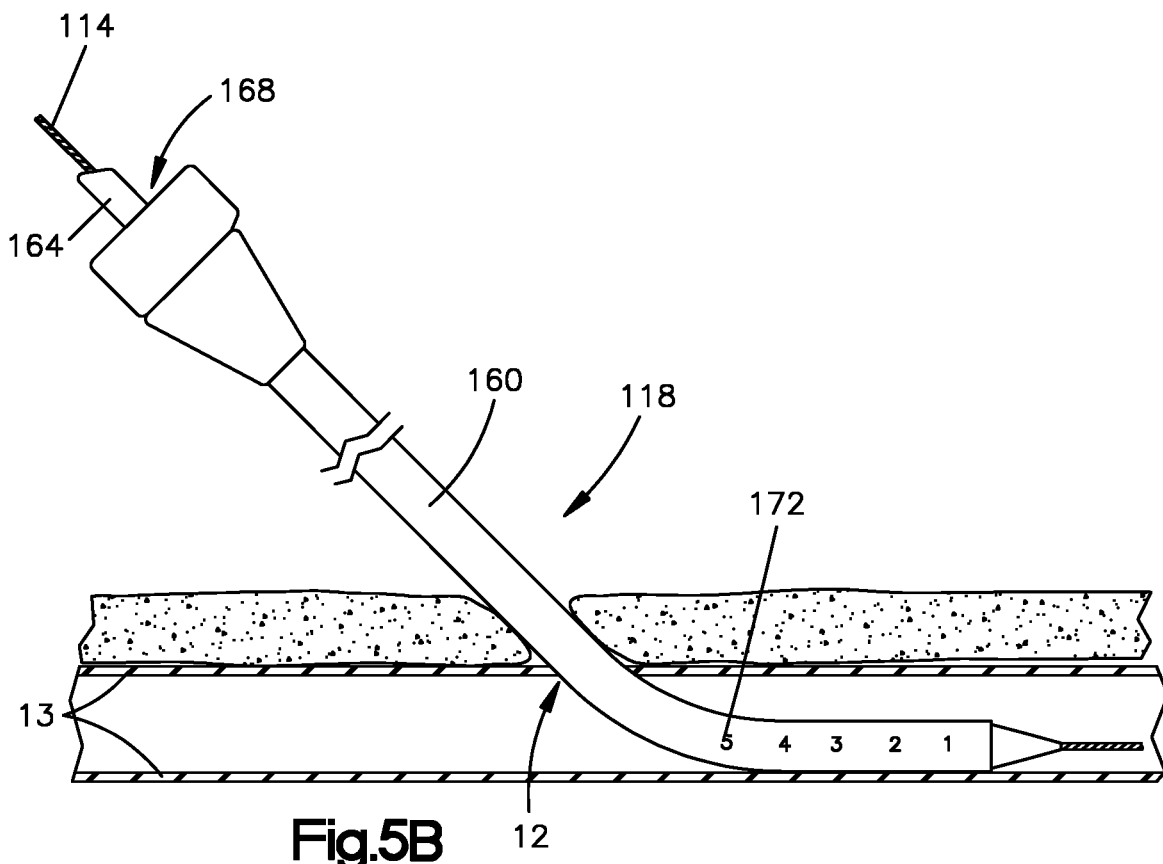
FIG. 5B is a schematic showing the access sheath of FIG. 4A being moved into the vessel.
Figure 5C:
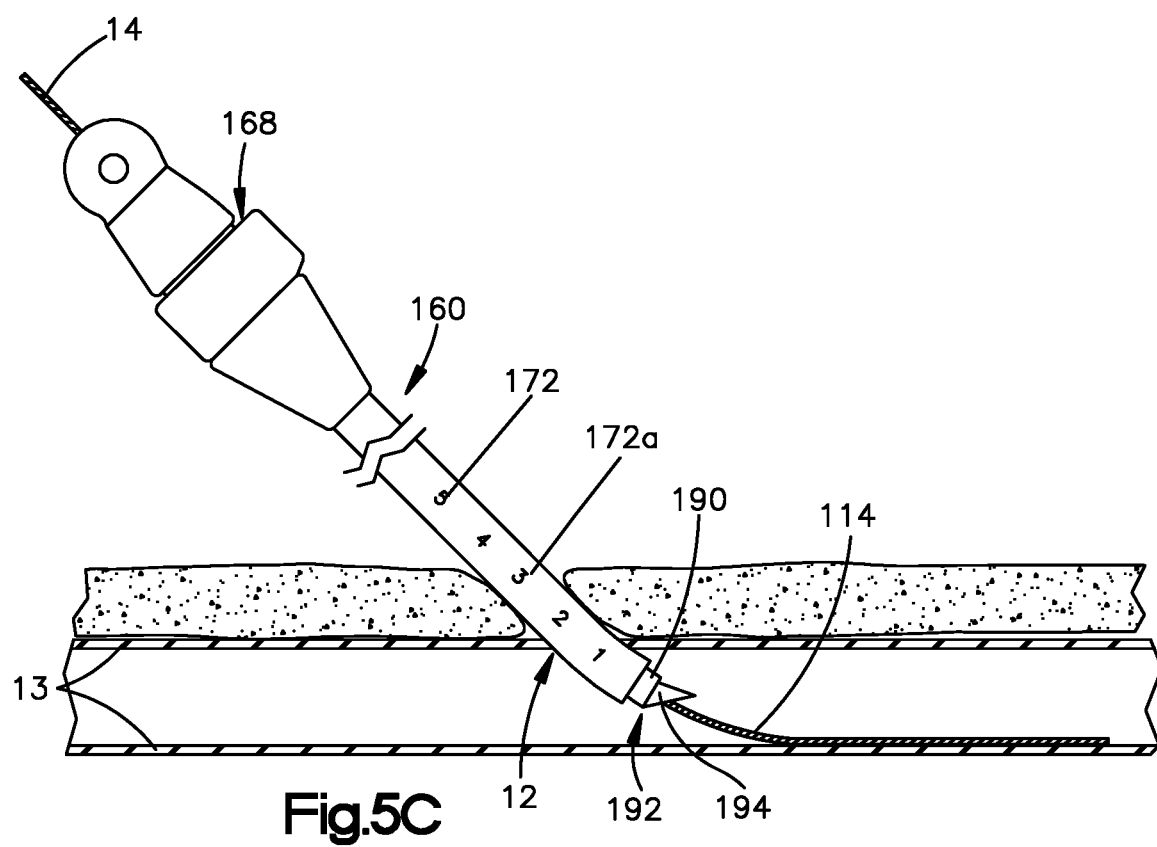
FIG. 5C is a schematic showing the sheath dilator removed from the access channel and the sheath body positioned such that a depth marking on the sheath body that corresponds to the at least one marking on the puncture locating dilator is visible above the surface of the skin.

Now referring to FIGS. 5A-5C, the guide wire 114 can be inserted through the puncture site 12 and into the vessel 13 such that a portion of the guide wire 114 protrudes from the vessel. Once the guide wire 114 is positioned, a proximal end of the guide wire 114 can be inserted into the distal end of the puncture locating dilator 110. As shown in FIG. 5A, the puncture locating dilator 110 can then be moved along the guide wire 114 until the distal end of the puncture locating dilator 110 and the blood inlet hole 142 enter the vessel 13 such that blood flows into the inlet hole 142 and out the outlet hole 146 to thereby locate a position of the puncture site 12. The position of the puncture site 12 can be confirmed via feedback of blood flow exiting the blood outlet hole 146 by alternatingly inserting and retracting the puncture locating dilator 10. As shown in FIG. 5A, after the position of the puncture site 12 has been located, a first visible marking 154a of the dilator 110 can be noted. That is a first visible marking 154a that is adjacent the patient's skin can be noted. It should be appreciated, that in some embodiments, the puncture locating dilator 110 can be positioned over the guide wire 114 prior to the guide wire being inserted into the vessel 13.

As shown in FIG. 5B, after the puncture locating dilator 110 has been removed from the guide wire 14 and any subsequent dilators have been removed, the access sheath 118 can be moved along the guide wire 114 toward the puncture site 12 such that the distal end of the access sheath 118 enters the vessel 13 through the puncture site 12. In particular, the proximal end of the guide wire 114 is inserted into the distal end of the sheath dilator 164. And then the sheath body 160 and sheath dilator 164 can be moved together along the guide wire 114 toward the puncture site 12. Once inserted, the sheath dilator 164 can be pulled proximally such that the sheath dilator 164 is removed from the access channel 168.

After the sheath dilator 164 has been removed, a vascular closure procedure can be performed through the access channel 168. Therefore, a closure device 190 can be moved into the access channel 168 until a distal portion 192 (e.g. at least a portion of a toggle 194) of the closure device 190 is distal to the distal end of the sheath body 160. As shown in FIG. 5C the access sheath 118 can then be moved such that a first visible marking 172a of the sheath body 160 that is visible adjacent the patient's skin corresponds with the noted first visible marking 154a of the puncture locating dilator 110. It should be appreciated, that the closure device 190 can be moved into the access channel 168 either prior to or after the positioning of the access sheath 118 such that the first visible marking 172 corresponds to the noted marking 154. When the access sheath 118 is properly positioned, the closure device 190 will be positioned such that the sealing procedure can be completed. It should be appreciated, that while in the illustrated embodiment, in some embodiment's the depth markings 172 are on the sheath body 160, the depth markings can be on the closure device 190, as desired. Furthermore, it should be appreciated, that in such embodiments, the access sheath 118 can be pulled completely out of the vessel 13 when the closure device 190 is properly positioned.

Figure 6:
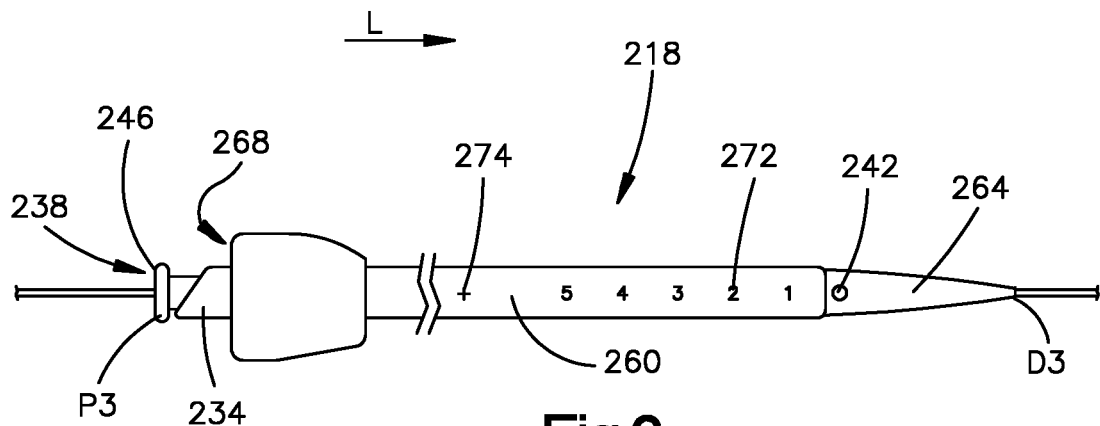
FIG. 6 is a top plan view, showing an access sheath of a puncture sealing system in accordance with another embodiment of the invention, the access sheath having a sheath body and a sheath dilator coupled within an access channel of the sheath body, the sheath body defining a plurality of depth markings and the sheath dilator including a blood inlet hole distal to the sheath body and a blood outlet hole proximal to the sheath body.
Figure 7A:
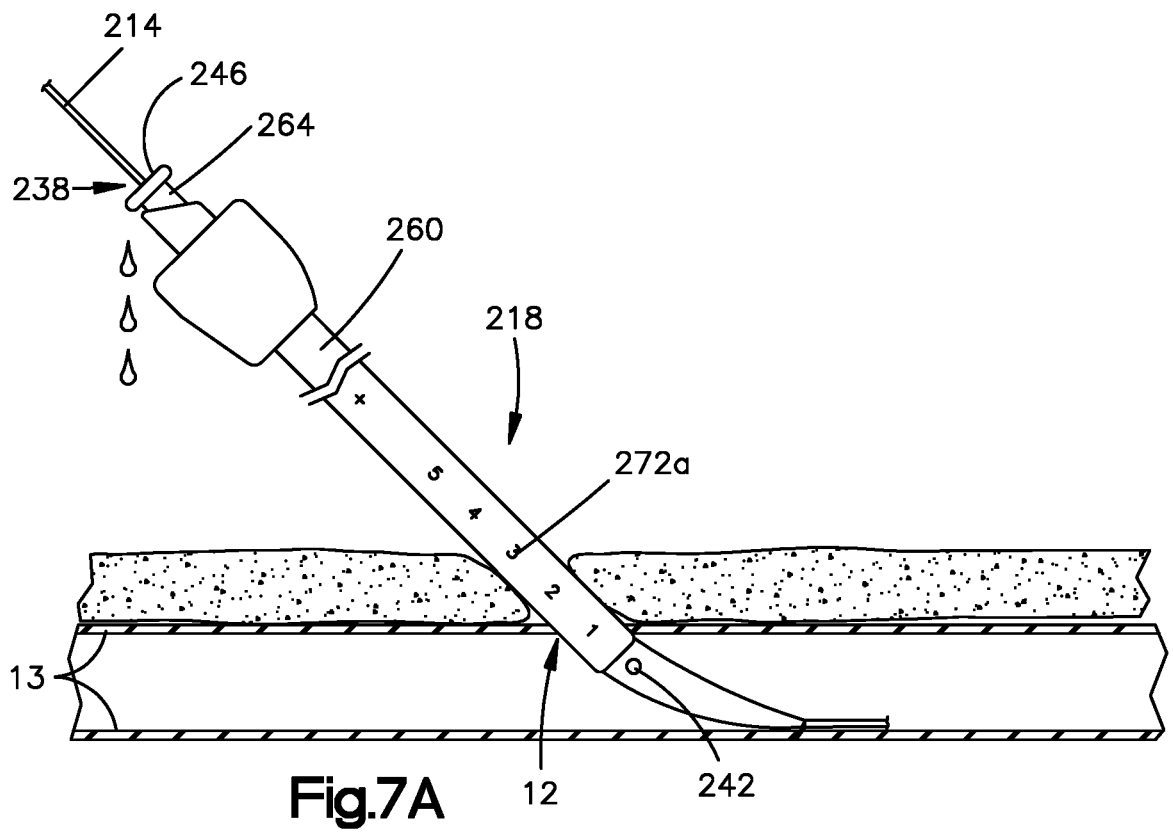
FIG. 7A is a schematic showing the access sheath of FIG. 6, positioned such that the inlet hole is disposed within a vessel proximate to a vessel puncture and at least one of the markings being visible above the surface of the skin.
Figure 7B:
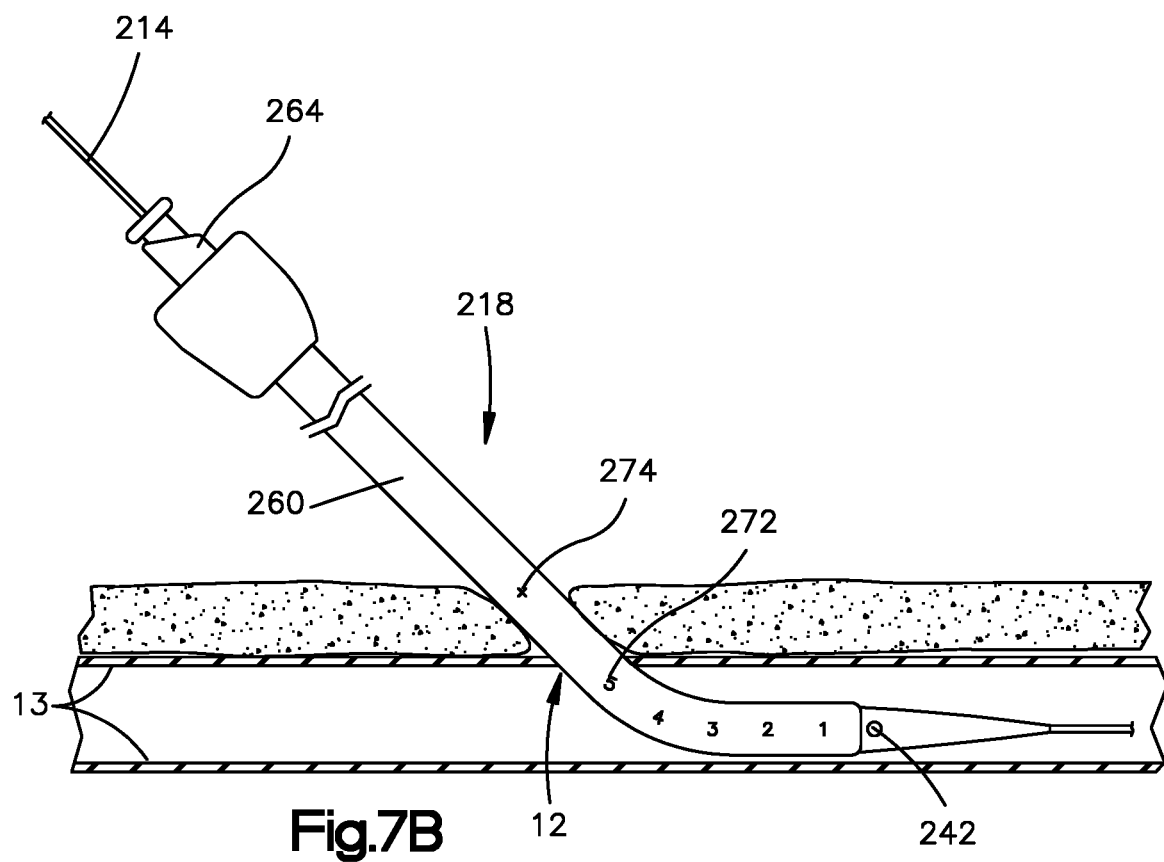
FIG. 7B is a schematic showing the access sheath of FIG. 7A, moved further into the vessel such that a full insertion marker on the sheath body that is proximal to the plurality of markings is adjacent the patient's skin.
Figure 7C:
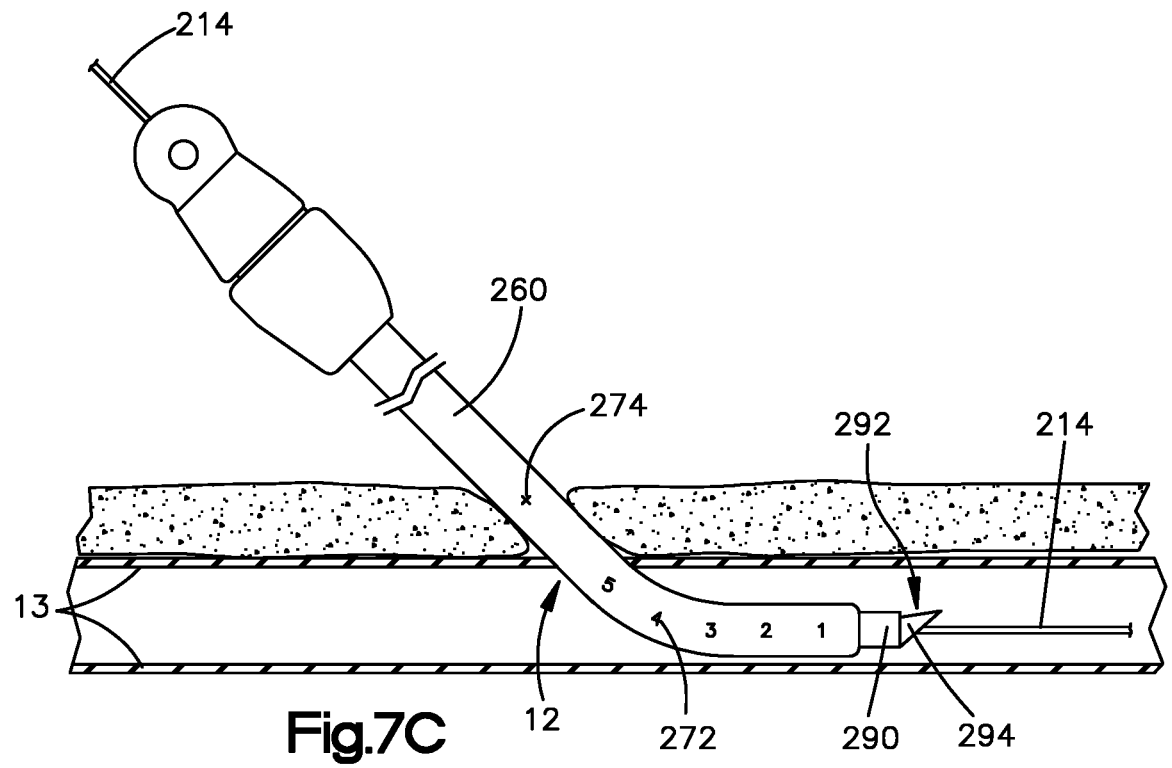
FIG. 7C is a schematic showing the access sheath of FIG. 7B with the sheath dilator removed from the access channel and a closure device moved into the access channel.
Figure 7D:
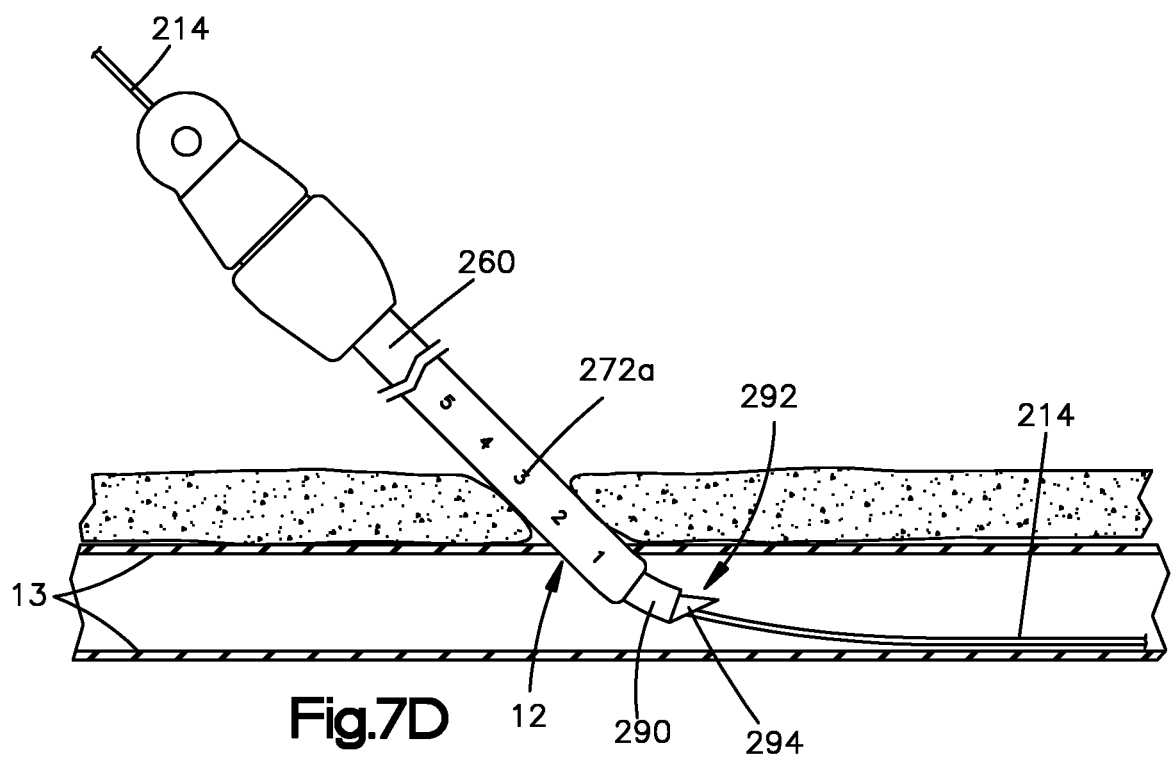
FIG. 7D is a schematic showing the access sheath of FIG. 7C moved proximally such that the at least one marking noted in FIG. 7A is again visible above the surface of the skin.

Now in reference to FIGS. 6-7D, a puncture sealing system in accordance with another embodiment of the invention can include an access sheath 218 having a sheath body 260 and a sheath dilator 264 coupled within an access channel 268 of the sheath body 260. The sheath dilator 264 can be configured as a puncture locating dilator such that the access sheath 218, itself is configured to determine the location of the puncture site 12. As in the embodiment shown in FIGS. 3A-5C, the sheath body 260 includes a plurality of depth markings that can be used to determine the location of the puncture site 12.

As shown in FIG. 6, the sheath body 260 is elongate along the first direction L and the access channel 268 extends through the sheath body 260 from a proximal end through to a distal end of the sheath body 260. The access channel 268 is configured to provide an access path to the puncture site 12 after the sheath dilator 264 has been removed from the access channel 268. The access sheath 218 is configured to be moved along the guide wire 214 toward the puncture site 12 such that the distal end of the access sheath 218 enters the vessel 13.

With continued reference to FIG. 6, the access sheath 218 further includes a plurality of depth markings 272 spaced from each other along the first direction L on the sheath body 260. The depth markings 272 are each spaced a respective distance from the distal end of the sheath body 260. Therefore, when the puncture site 12 is located with the sheath dilator 264, a first marking of the plurality of depth markings 272 can be noted to thereby indicate to a user the location of the puncture site 12 relative to the distal end of the sheath body 260. In the illustrated embodiment, the depth markings 272 are numbers. It should be appreciated, however, that the depth markings 272 can have other configurations as desired. As will be described, the depth markings 272 can be used to position the sheath body 260.

With continued reference to FIG. 6, the access sheath 218 can further include a full insertion marker 274 on the sheath body 260 that is proximal to the plurality of markings 272. The full insertion marker 274 can be positioned on the sheath body 260 to indicate to a surgeon when the access sheath 218 is sufficiently positioned so that for example the sheath dilator 264 can be removed from the sheath body 260. The full insertion marker 274 can be a number like the depth markers 172 or can be a symbol as desired. It should be appreciated, however, that the full insertion marker 274 can also be a furthest depth marker of the plurality of depth markers 272 from the distal end of the sheath body 260, as desired.

The sheath dilator 264 is similar to the sheath dilator 10 and operates in a similar manner. As shown in FIG. 6, the sheath dilator 264 includes a dilator body 234 that is elongate along a first direction L and defines a proximal end $P_3$ and a distal end $D_3$ that is spaced from the proximal end $P_3$ along the first direction L. The sheath dilator 264 defines a guide channel 238 that extends through the dilator body 234 along the first direction L from the distal end $D_3$ through to the proximal end $P_3$. The guide channel 238 is configured to receive the guide wire 214 such that the sheath dilator 264 and sheath body 260 can be moved along the guide wire 214 toward the puncture site 12. The guide channel 238 at the distal end $D_3$ can have a diameter that is substantially equal to that of the guide wire 214 so that the sheath dilator 264 can move along the guide wire 214 in a controlled manner. As shown in FIG. 6, the sheath dilator 264 can further define a blood inlet hole 242 that extends through the dilator body 234 along a direction that is transverse to the first direction L, and a blood outlet hole 246 that extends through the dilator body 234 proximal to the blood inlet hole 242. The blood inlet hole 242 and the blood outlet hole 246 are in fluid communication with each other such that when the blood inlet hole 242 enters the vessel 13, blood from the vessel 13 will enter the blood inlet hole 242 and exit the blood outlet hole 246 to thereby indicate that the blood inlet hole 242 has entered the vessel 13. In this way, a position of the puncture site 12 can be located or otherwise determined. In the illustrated embodiment, the blood inlet and outlet holes 242 and 246 extend into the guide channel 238 such that blood entering the blood inlet hole 242 will travel through the guide channel 238, around the guide wire 214, and out the blood outlet hole 246. It should be appreciated, however, that in some embodiments, the guide channel 238 and the channel through which the blood flows can be separate and distinct from each other, as desired.

After the puncture site has been located using the sheath dilator 264, a first visible marking 272a on the sheath body 260 that is adjacent the patient's skin can be noted. And after the puncture site has been located and its position noted, the sheath dilator 264 can be pulled proximally from the access channel 268.

Now referring to FIGS. 7A-7D, the guide wire 214 can be inserted through the puncture site 12 and into the vessel 13 such that a portion of the guide wire 214 protrudes from the vessel. Once the guide wire 214 is positioned, a proximal end of the guide wire 214 can be inserted into the distal end of the sheath dilator 264. As shown in FIG. 7A, the sheath dilator 264 along with the sheath body 260 can then be moved along the guide wire 214 until the distal end of the sheath dilator 264 and the blood inlet hole 242 enter the vessel 13 such that blood flows into the inlet hole 242 and out the outlet hole 246 to thereby locate a position of the puncture site 12. The position of the puncture site 12 can be confirmed via feedback of blood flow exiting the blood outlet hole 246 by alternatingly inserting and retracting the sheath dilator 264 and sheath body 260 combination. As shown in FIG. 7A, after the position of the puncture site 12 has been located, a first visible marking 272a of the sheath body 260 can be noted. That is, a first visible marking 272a that is adjacent the patient's skin can be noted. It should be appreciated, that in some embodiments, the access sheath 218 can be positioned over the guide wire 214 prior to the guide wire being inserted into the vessel 13.

As shown in FIG. 7B, after the first visible depth marking 272a has been noted, the access sheath 218 can be further moved along the guide wire 214 until the full insertion marker 274 is adjacent the patient's skin surface. At this time, the sheath dilator 264 can be pulled proximally and removed from the access channel 268. And after the sheath dilator 264 has been removed, a vascular closure procedure can be performed through the access channel 268. Therefore, as shown in FIG. 7C a closure device 290 can be moved into the access channel 268 until a distal portion 292 of the closure device is distal to the distal end of the sheath body 260 and the closure device 290 couples to the sheath body via for example a snap fit. For example, at least a portion of a toggle 294 of the closure device can be distal to the sheath body 260 when the closure device 290 is positioned within the access channel 268. As shown, in FIG. 7C, the closure device 290 can be moved along the guide wire 214 as it is being inserted into the access channel 268.

As shown in FIG. 7D, the sheath body 260 and closure device 290 can then be pulled proximally until the depth marking 272a noted during the puncture locating step becomes visible adjacent the patient's skin. When the access sheath 218, or at least the sheath body 260 is properly positioned, the closure device will be positioned such that the sealing procedure can be completed. For example, the toggle 294 can be deployed into the vessel 13 so that the puncture site 12 can be sealed. It should be appreciated, that in some embodiments the closure device 290 can include the depth markings and the sheath body 260 can be pulled such that the sheath body 260 exits the vessel 13 and a first depth marking on the closure device 290 that corresponds to the noted depth marking is visible.

Now in reference to FIGS. 8A-9F, a puncture sealing system in accordance with another embodiment of the invention can include an access sheath 318 having a sheath body 360 and a sheath dilator 364 coupled within an access channel 368 of the sheath body 360. The access sheath 318 can further include a syringe 366 that is coupled to the sheath body 360 and is configured to aid in determining the location of the puncture site 12. As in the embodiment shown in FIGS. 6-7D, the sheath body 360 includes a plurality of depth markings that can be used to determine the location of the puncture site 12.

Figure 8A:
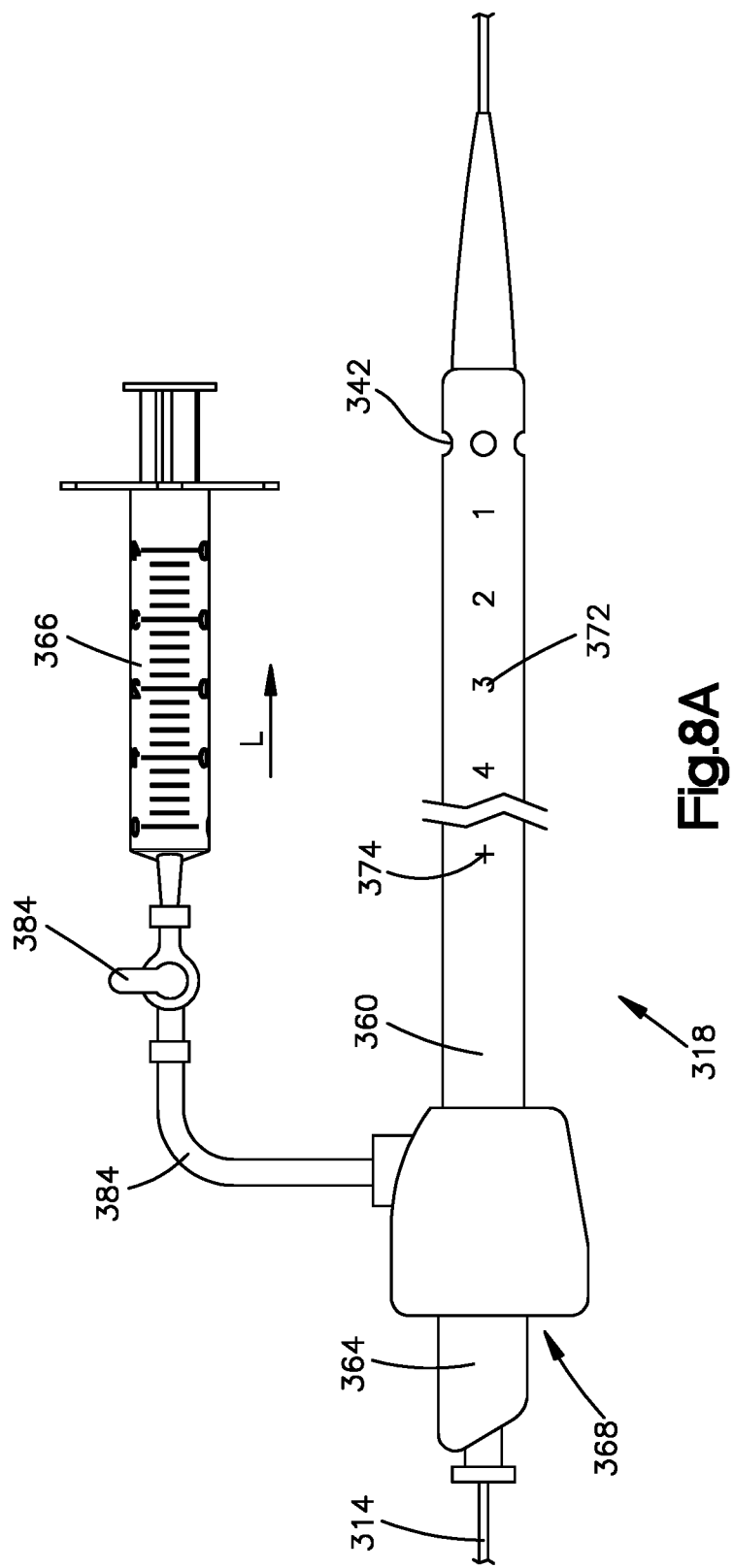
FIG. 8A is a top plan view, showing an access sheath of a puncture sealing system in accordance with another embodiment of the invention, the access sheath including a sheath body and a sheath dilator coupled within an access channel of the sheath body.

As shown in FIGS. 8A and 8B, the sheath body 360 is elongate along the first direction L and the access channel 368 extends through the sheath body 360 from a proximal end through to a distal end of the sheath body 360. The access channel 368 is configured to provide an access path to the puncture site 12 after the sheath dilator 364 has been removed from the access channel 368. The access sheath 318 is configured to be moved along the guide wire 314 toward the puncture site 12 such that the distal end of the access sheath 318 enters the vessel 13.

With continued reference to FIGS. 8A and 8B, the access sheath 318 further includes a plurality of depth markings 372 spaced from each other along the first direction L on the sheath body 360. The depth markings 372 are each spaced a respective distance from the distal end of the sheath body 360. Therefore, when the puncture site 12 is located, a first marking of the plurality of depth markings 372 can be noted to thereby indicate to a user the location of the puncture site 12 relative to the distal end of the sheath body 360. In the illustrated embodiment, the depth markings 372 are numbers. It should be appreciated, however, that the depth markings 372 can have other configurations as desired. As will be described, the depth markings 372 can be used to position the sheath body 360.

With continued reference to FIGS. 8A and 8B, the access sheath 318 can further include a full insertion marker 374 on the sheath body 360 that is proximal to the plurality of markings 372. The full insertion marker 374 can be positioned along the sheath body 360 to indicate to a surgeon when the access sheath 318 is sufficiently positioned so that the sheath dilator 364 can be removed from the sheath body 360. The full insertion marker can be a number like the depth markers 372 or can be a symbol as desired. It should be appreciated, however, that the full insertion marker 374 can also be a furthest depth marker of the plurality of depth markers 372 from the distal end of the sheath body 360, as desired.

As shown in FIG. 8B, the access sheath 318 can further include at least one such as a plurality of blood inlet holes 342 that extend through the sheath body 360 and into the access channel 368. The blood inlet holes 342 are disposed distal to the depth markings 372 and are adjacent the distal end of the sheath body 360. The blood inlet holes 342 are in communication with the syringe 366 such that when the blood inlet holes 342 are positioned within the vessel 13, blood from the vessel can be withdrawn by the syringe 366. In particular, the syringe 366 can be releasably attached to a tube 380 that extends from the sheath body 360. The tube 380 can include a valve 384 that is configured to have an open position whereby blood can exit the tube 380 into the syringe 366 and a closed position whereby blood is unable to exit the tube 380. When in the closed position, the syringe 366 can be removed.

Now referring to FIG. 8C, the sheath dilator 364 includes a dilator body 334 that is elongate along a first direction L and defines a proximal end $P_4$ and a distal end $D_4$ that is spaced from the proximal end $P_4$ along the first direction L. The sheath dilator 364 defines a guide channel 338 that extends through the dilator body 334 along the first direction L from the distal end $D_4$ through to the proximal end $P_4$. The guide channel 338 is configured to receive the guide wire 314 such that the sheath dilator 364 and sheath body 360 can be moved along the guide wire 314 toward the puncture site 12. The guide channel 338 at the distal and proximal ends $D_4$ and $P_4$ can have a diameter that is substantially equal to that of the guide wire 314 so that the sheath dilator 364 can move along the guide wire 314 in a controlled manner. As shown in FIG. 8C, the sheath dilator 364 can further define a plurality of fluid channels 346 that are configured to be a conduit that directs blood from the inlet holes 342 to an outlet hole that is in fluid communication with the tube 380. As shown in FIG. 8C, the fluid channels 346 are elongate along the first direction L and are in communication with respective blood inlet holes 342 when the sheath dilator 360 is coupled within the access channel 368. The blood inlet holes 342 and the syringe 366 are in fluid communication with each other such that when the blood inlet holes 342 enter the vessel 13, blood from the vessel 13 can be withdrawn from the vessel by the syringe 366 thereby indicating that at least one of the blood inlet holes 342 has entered the vessel 13. In this way, a position of the puncture site 12 can be located or otherwise determined.

After the puncture site has been located using the syringe 366, a first visible marking 372a on the sheath body 360 that is adjacent the patient's skin can be noted. And after the puncture site has been located and its position noted, the sheath dilator 364 can be pulled proximally from the access channel 368.

Figure 9A:
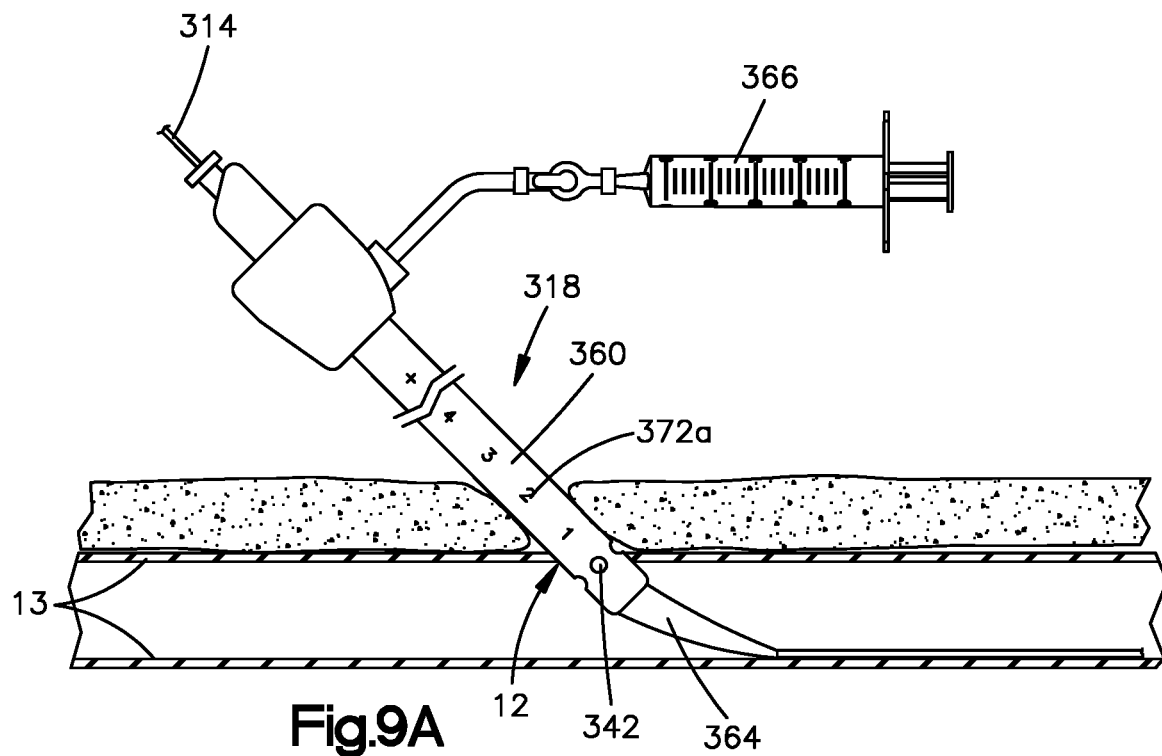
FIG. 9A is a schematic showing the access sheath of FIG. 8A, positioned such that the blood inlet hole is disposed within a vessel proximate to a vessel puncture such that the syringe can withdraw blood through the blood inlet holes, and at least one of the markings being visible above the surface of the skin.

Now referring to FIGS. 9A-9F, the guide wire 314 can be inserted through the puncture site 12 and into the vessel 13 such that a portion of the guide wire 314 protrudes from the vessel. Once the guide wire 314 is positioned, a proximal end of the guide wire 314 can be inserted into the distal end of the sheath dilator 364. As shown in FIG. 9A, the sheath dilator 364 along with the sheath body 360 can then be moved along the guide wire 314 until the distal end of the sheath dilator 364 and the blood inlet holes 342 enter the vessel 13. Once positioned, the syringe 366 can be actuated so as to draw blood from the vessel 13, through the fluid flow channels of the sheath dilator 364 and into the syringe 366.

Figure 9B:
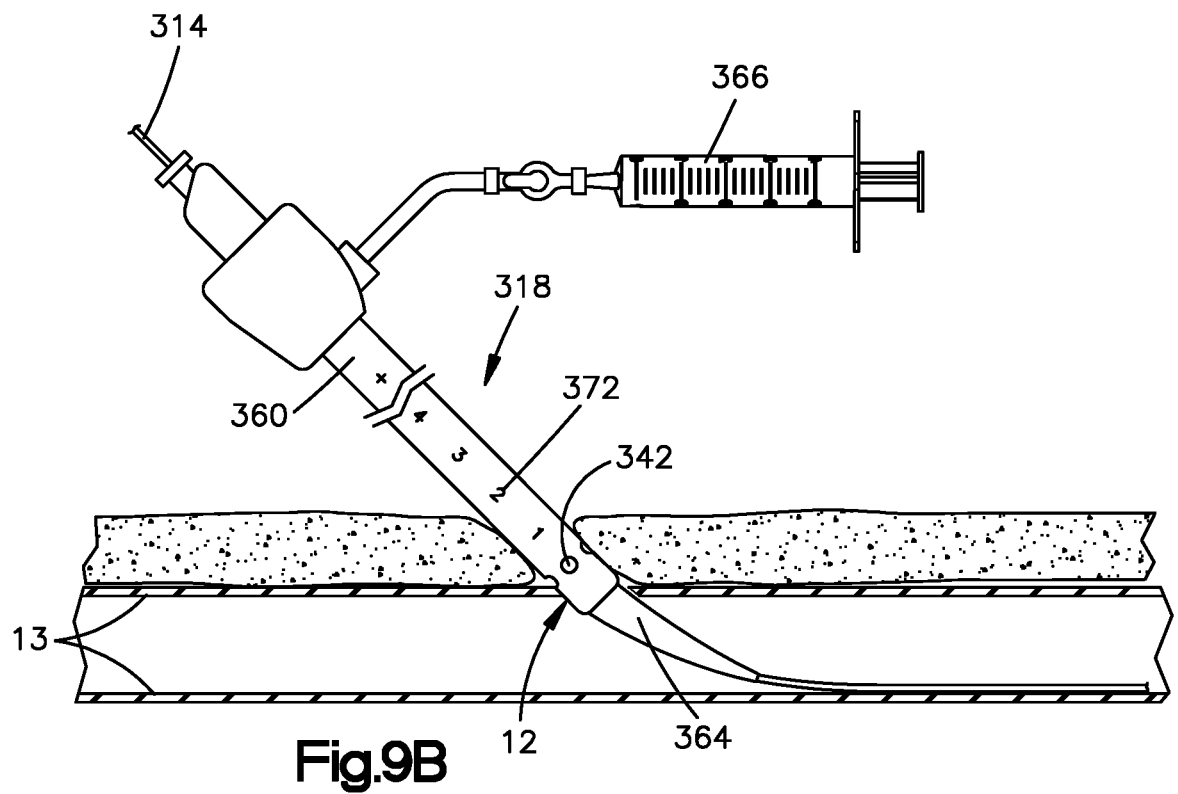
FIG. 9B is a schematic showing the access sheath of FIG. 9A in a position such that the syringe can no longer withdraw blood through the inlet holes.

Once it has been confirmed that the blood inlet holes 342 are within the vessel, the sheath dilator 364 and the sheath body 360 combination can be slightly withdrawn proximally along the guide wire 314. Again, the syringe 366 can be actuated to determine whether the blood inlet holes 342 are still within the vessel 13. As shown in FIG. 9B, the withdrawing and actuating steps can be repeated until the inlet holes 342 are external to the vessel 13 such that fluid flow to the syringe 366 is not possible or significantly slowed when the syringe 366 is actuated. It should be appreciated, that the syringe 366 can be actuated by drawing blood from the vessel 13 only or by drawing blood from the vessel 13 and subsequently purging it back into the vessel 13, as desired.

After it has been determined that the blood inlet holes 342 are external to the vessel 13, the sheath dilator 364 and sheath body combination 360 can be slightly moved distally along the guide wire 314 to thereby again position the inlet holes 342 within the vessel 13 as shown n FIG. 9A. The syringe 366 can once again be actuated to confirm that the inlet holes 342 are positioned within the vessel 13. At this time, after the position of the puncture site 12 has been located, the first visible marking 372a of the sheath body 360 can be noted. That is, a first visible marking 372 that is adjacent the patient's skin can be noted.

Figure 9C:
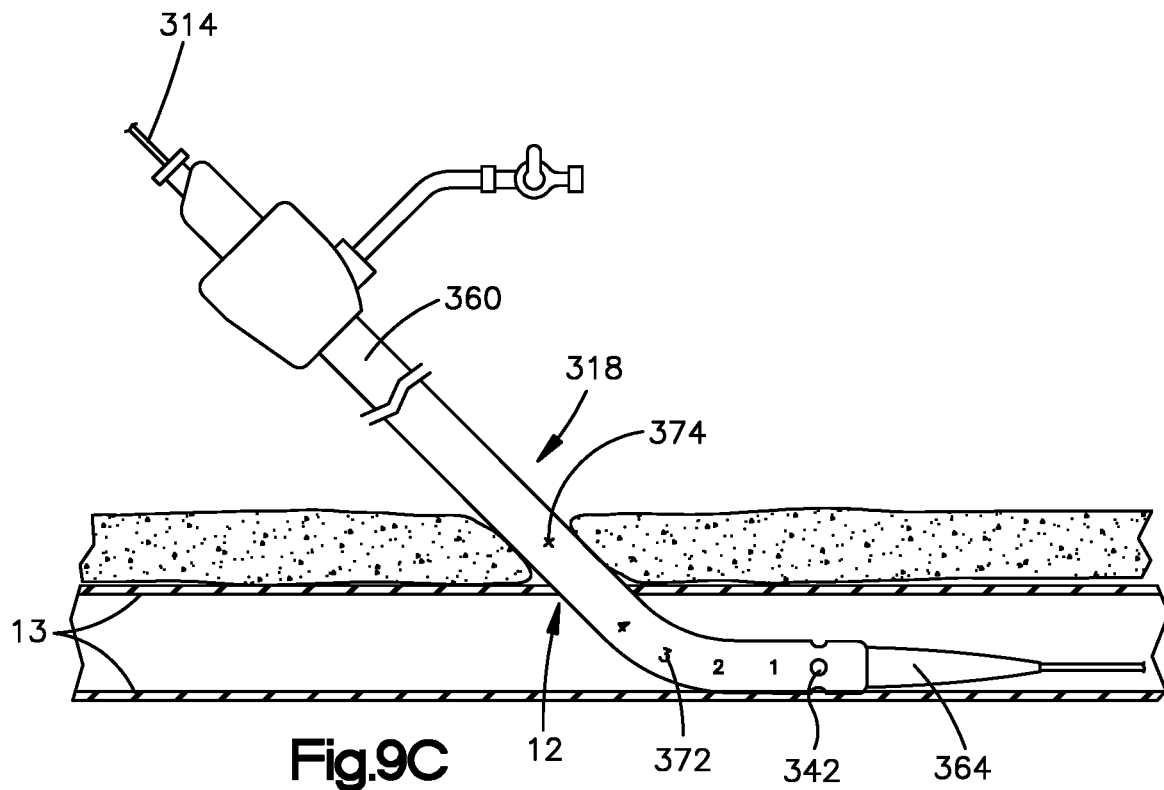
FIG. 9C is a schematic showing the access sheath of FIG. 9B, moved further into the vessel such that a full insertion marker on the sheath body that is proximal to the plurality of markings is adjacent the patient's skin.
Figure 9D:
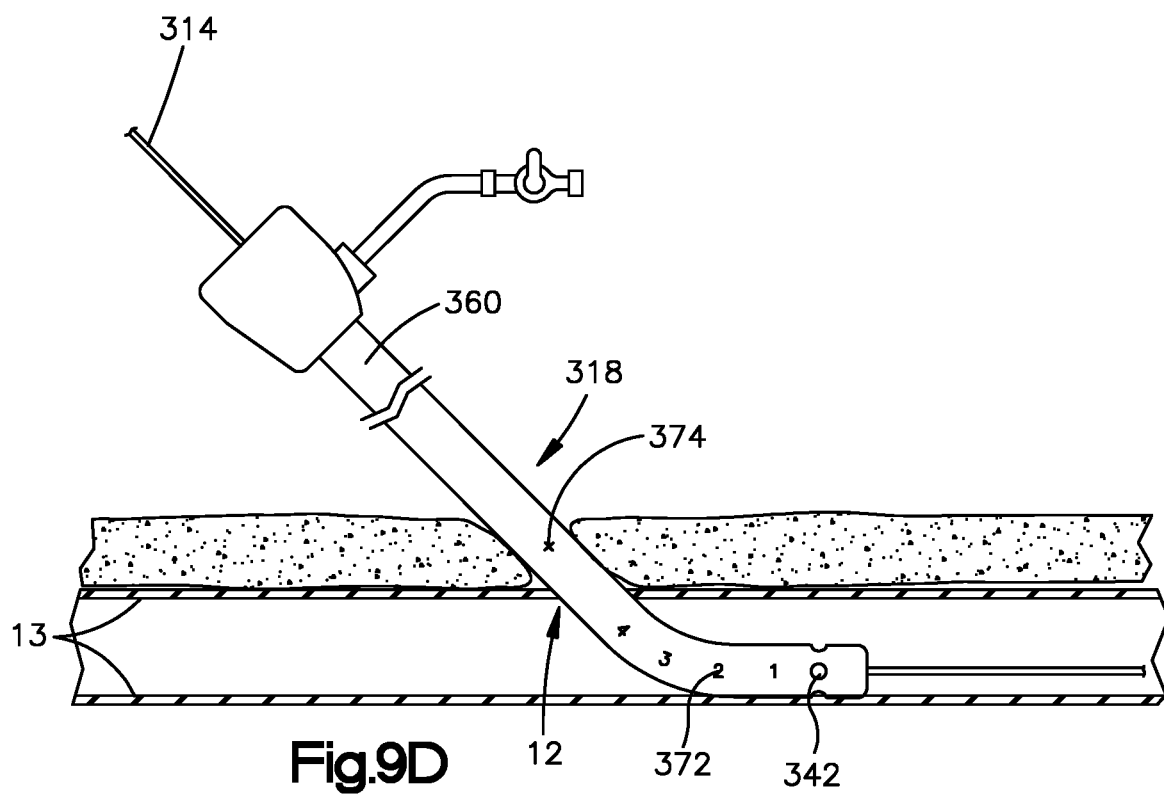
FIG. 9D is a schematic showing the access sheath of FIG. 9C with the sheath dilator removed from the access channel.
Figure 9E:
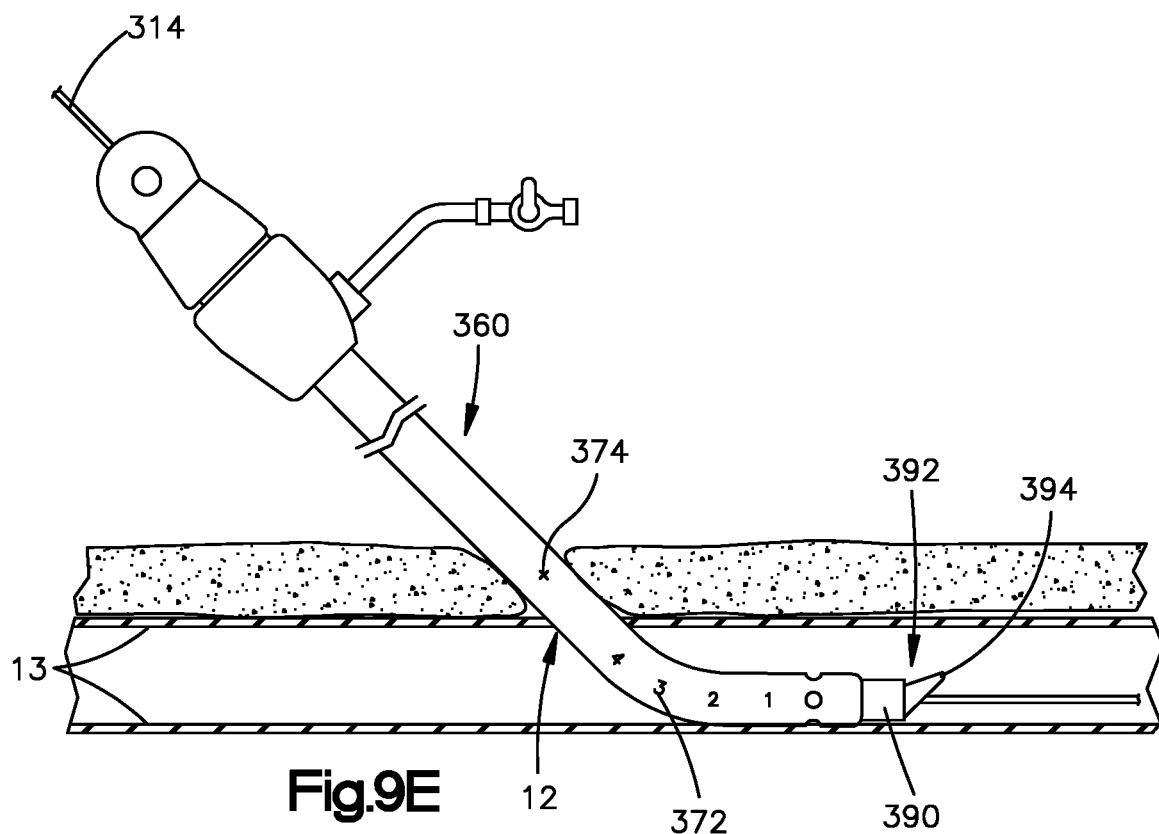
FIG. 9E is a schematic showing the access sheath of FIG. 9D with a closure device coupled within the access channel.

As shown in FIGS. 9C and 9D, after the first visible depth marking 372 has been noted, the syringe 366 can be removed and the access sheath 318 can be further moved along the guide wire 314 until the full insertion marker 374 is adjacent the patient's skin surface. At this time, the sheath dilator 364 can be pulled proximally and removed from the access channel 368 as shown in FIG. 9D. And after the sheath dilator 364 has been removed, a vascular closure procedure can be performed through the access channel 368. Therefore, as shown in FIG. 9E a closure device 390 can be moved into the access channel 368 until a distal portion 392 of the closure device is distal to the distal end of the sheath body 360 and the closure device 390 couples to the sheath body. For example, at least a portion of a toggle 394 of the closure device can be distal to the sheath body 360 when the closure device 390 is positioned within the access channel 368. As shown, in FIG. 9E, the closure device 390 can be moved along the guide wire 314 as it is being inserted into the access channel 368. It should be appreciated, however, that in some embodiments, the guide wire 314 is removed along with the sheath dilator 364. And in such an embodiment, the closure device 390 is positioned within the access channel 318 without the use of a guide wire 314.

Figure 9F:
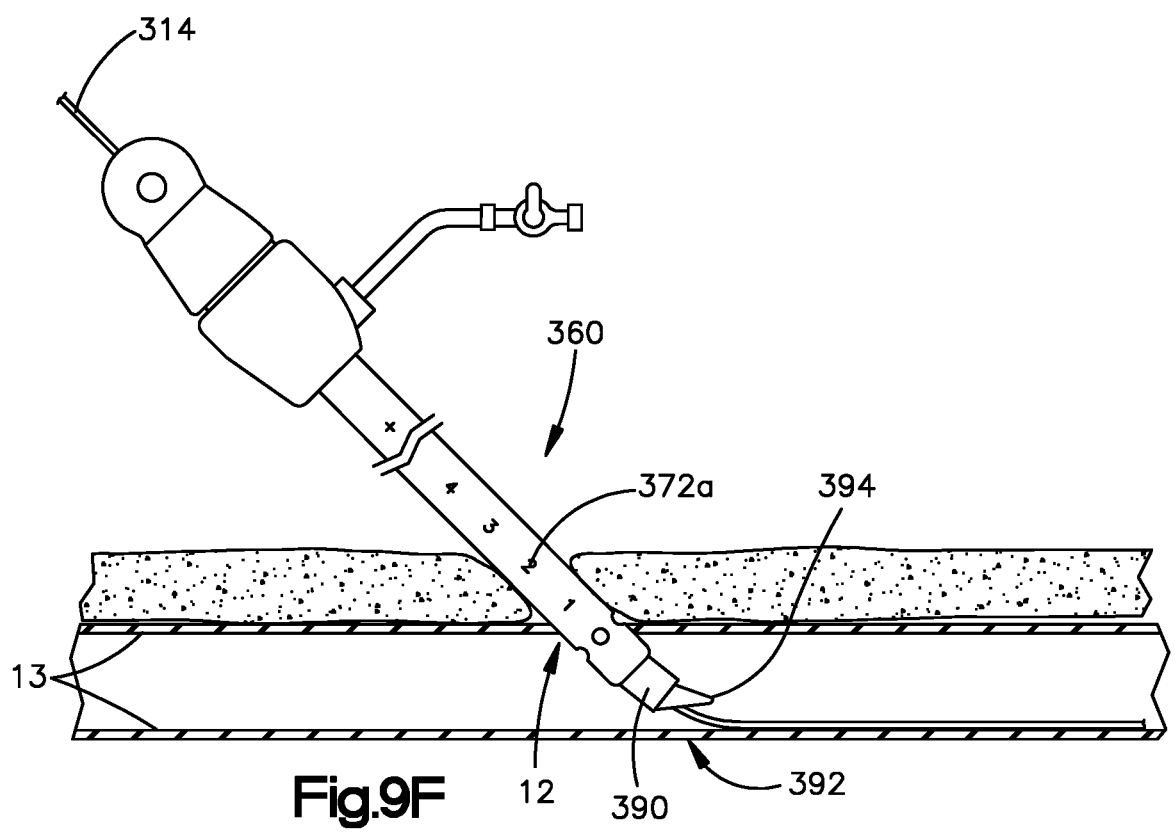
FIG. 9F is a schematic showing the access sheath of FIG. 7C moved proximally such that the at least one marking is again visible above the surface of the skin.

As shown in FIG. 9F, the sheath body 360 and closure device 390 can then be pulled proximally until the depth marking 372a noted during the puncture locating step becomes visible adjacent the patient's skin. When the access sheath 318 or at least the sheath body 360 is properly positioned, the closure device will be positioned such that the sealing procedure can be completed. For example, the toggle 394 can be deployed into the vessel 13 so that the puncture site 12 can be sealed. It should be appreciated, that in some embodiments the closure device 390 can include the depth markings and the sheath body 360 can be pulled such that the sheath body 360 exits the vessel 13 and a first depth marking on the closure device 390 that corresponds to the noted depth marking is visible.

Figure 10A:
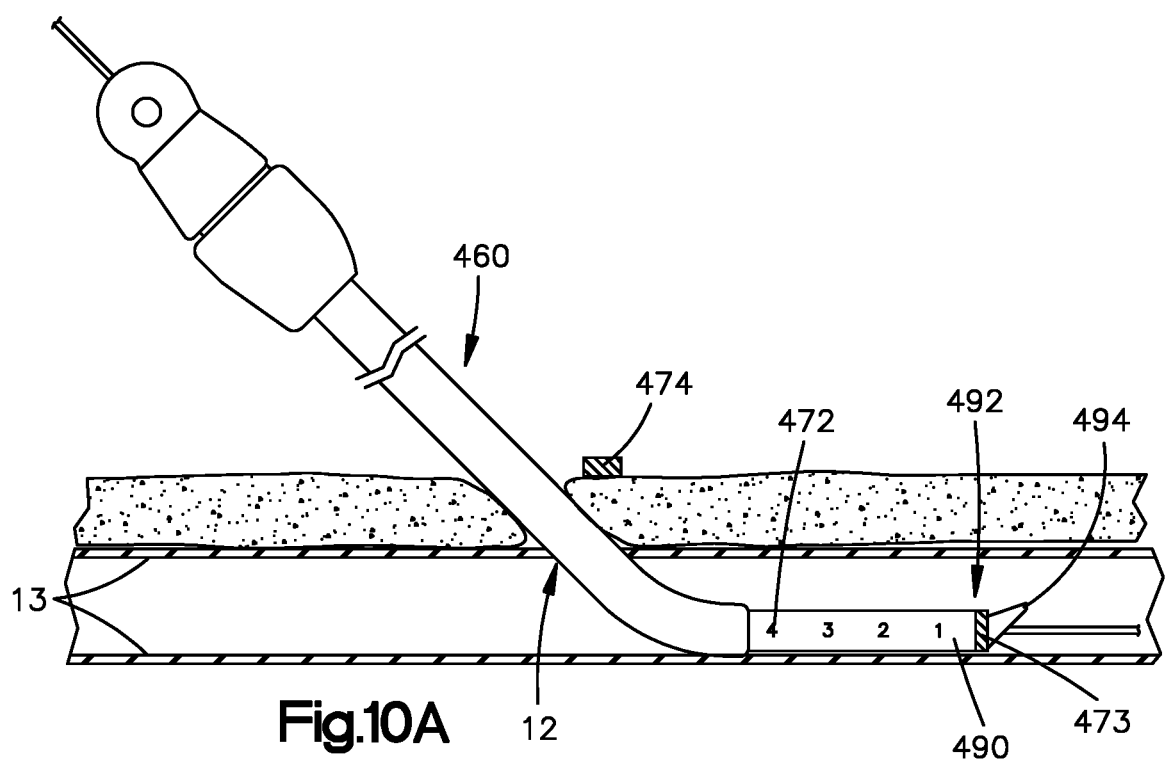
FIG. 10A is a schematic showing a closure device coupled within an access channel of a sheath body, the closure device having a plurality of depth markings.
Figure 10B:
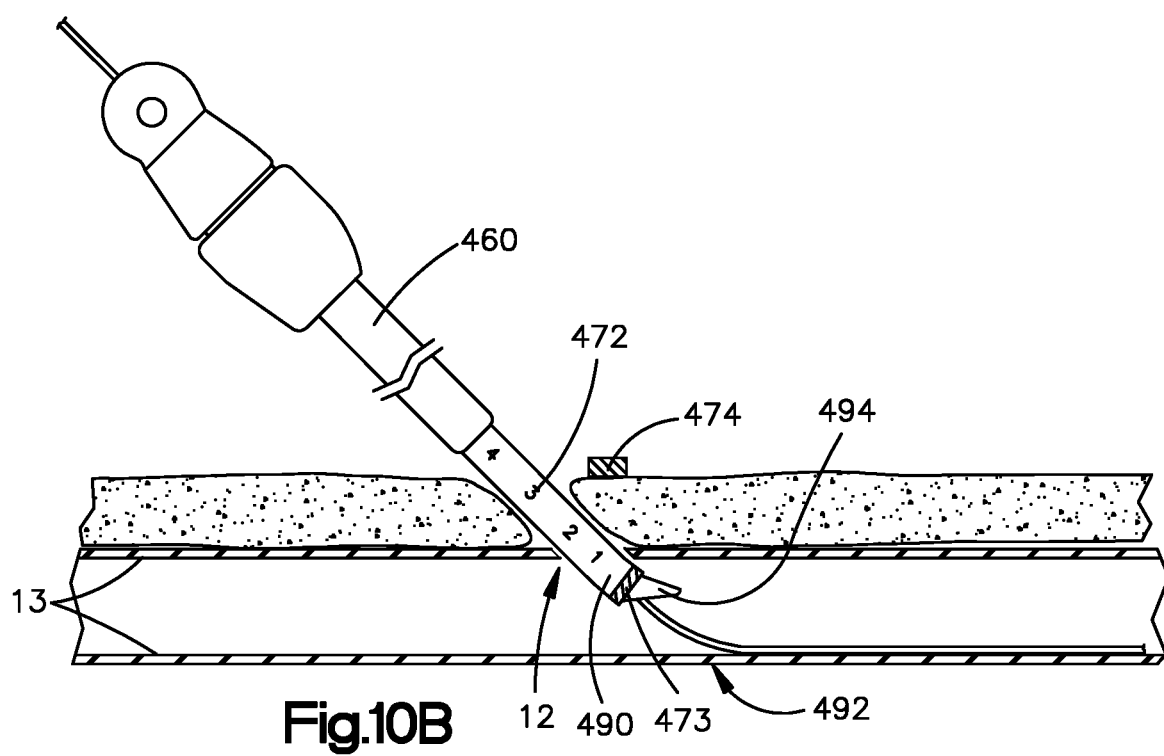
FIG. 10B is a schematic showing the closure device and sheath body combination of FIG. 10A moved such that a depth marking of the closure device that corresponds to a previously noted depth marking is the first visible depth marking adjacent the patient's skin.

FIGS. 10A and 10B show an embodiment whereby the closure device includes the depth markings and/or radiopaque marker and the sheath body is pulled completely out of the vessel when the closure device is being aligned. As shown in FIG. 10A, a closure device 490 can be moved into a sheath body 460 such that the closure device 490 extends out a distal end of the sheath body 460. In particular, the closure device 490 can be moved into the access channel of the sheath body 460 such that the closure device couples to the sheath body and a plurality of depth markings 472 on the closure device 490 are exposed distal to the sheath body 460. Once the closure device 490 is coupled to the sheath body 460, the sheath body can be pulled proximally such that the sheath body 460 exits the vessel 13 and such that a first depth marking on the closure device 490 that corresponds to the depth marking noted during location of the puncture site is visible adjacent the patient's skin. At this point the closure device 490 will be in position to seal the puncture site. It should be appreciated, however, that the closure device 490 can alternatively or in addition to include a radiopaque band 473 that can be used to position the closure device 490 by aligning the radiopaque band 473 with an external marker 474. It should also be appreciated, that while sheath body 460 has been completely removed from the vessel 13 when the closure device 490 is positioned, in some embodiments, the sheath body 460 can remain within the vessel 13 when the closure device 490 is positioned.

While the foregoing description and drawings represent the preferred embodiment of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art. For example, the device shown in FIG. 6 can include a sheath body that defines a blood inlet hole similar to the embodiment shown in FIG. 8A. Further, it should be appreciated, that in some embodiments, the guide wire is removed along with the sheath dilator. And that in such an embodiment, the closure device is positioned within the access channel without the use of a guide wire.

What is claimed:

1. A vascular location system, comprising:
    a dilator that is elongate along a first longitudinal direction, the dilator having a distal end, a proximal end spaced from the distal end along the first longitudinal direction, an outer surface, an inlet hole spaced from the distal end of the dilator, an outlet hole in communication with the inlet hole disposed between the proximal end and the inlet hole, and a first plurality of depth markings on the outer surface disposed between the inlet hole and the outlet hole, wherein the plurality of depth markings are spaced from each other along the longitudinal direction; and
    an access sheath that is elongate along a second longitudinal direction, the access sheath having a distal end, a proximal end spaced from the distal end of the access sheath along the second longitudinal direction, a sheath inner surface, a sheath outer surface opposite the sheath inner surface, an access channel that extends from the distal end of the access sheath to the proximal end of the access sheath, wherein the access channel is configured to receive the dilator, and a second plurality of depth markings on the outer surface of the access sheath,
    wherein a first depth of marking of the first plurality of depth markings on the dilator corresponds to a first depth marking of the second plurality of depth markings, such that, the first plurality of depth markings are indicative of a depth the dilator is inserted into a puncture and the second plurality of marking are indicative of the depth that the access sheath is inserted into the puncture.

2. The system of claim 1, wherein the first plurality of depth markings along the dilator are a plurality of numbers, and the second plurality of depth markings along the access sheath are a plurality of numbers.

3. The system of claim 1, further comprising a guide channel that extends from the distal end to the proximal end, wherein the guide channel is configured to receive a guide wire as the dilator is placed along the guidewire into the puncture.

4. The system of claim 3, wherein the inlet hole is open to the guide channel and the outlet hole is open to the guide channel such a blood entering blood entering the inlet hole travels through the guide channel and out the outlet hole.

5. The system of claim 3, further comprising a channel that is open to the inlet hole and the outlet hole, wherein the channel is separate and distinct from the guide channel.

6. The system of claim 1, wherein the plurality of depth markings on the dilator are configured to allow a user to visually note a depth or a puncture in the vessel relative to a patient's skin surface.

7. The system of claim 1, wherein the access sheath includes a sheath body having an access channel, and a sheath dilator disposed within an access channel of the sheath body.

8. The system of claim 1, further comprising:
a vascular closure device configured to be inserted into the access channel of the sheath body until a distal portion of the closure device is distal to the distal end of the sheath body, wherein the vascular closed device defines an internal lumen sized to receive and surround a guide wire such that the vascular closure device is slidable along the guidewire.

9. The system of claim 8, wherein the sheath body includes a hub, and the vascular closure device is configured to be fully seated in access sheath, such that the vascular closure device mechanically coupled to the hub of the access sheath, and a distal portion of the vascular closure device extends out the distal end of the access sheath.

10. The system of claim 8, wherein the vascular closure device includes a suture, a toggle coupled to the suture, a plug disposed along the suture, and a locking member coupled to the suture and slidable along the suture to secure the plug against the toggle in a compressed configuration.

\* \* \* \* \*